(12) United States Patent
Poole et al.

(10) Patent No.: US 11,986,988 B1
(45) Date of Patent: May 21, 2024

(54) NON-CROSSLINKED HEAT SHRINK TUBING

(71) Applicant: ZEUS COMPANY INC., Orangeburg, SC (US)

(72) Inventors: Tyler Poole, Lexington, SC (US); John Richard Campanelli, West Columbia, SC (US); Robert L. Ballard, Lexington, SC (US); Cameron Hunter, Saint Matthews, SC (US); Justin Marro, Orangeburg, SC (US); Parastoo Azamian, West Columbia, SC (US); Jacob Coleman, Lexington, SC (US); Shannon M. Giovannini, Columbia, SC (US); Patrick Cooper, Orangeburg, SC (US); James Michael Brown, St. Matthews, SC (US)

(73) Assignee: Zeus Company LLC, Orangeburg, SC (US)

( * ) Notice: Subject to any disclaimer, the term of this patent is extended or adjusted under 35 U.S.C. 154(b) by 0 days.

(21) Appl. No.: 17/985,247

(22) Filed: Nov. 11, 2022

(51) Int. Cl.
*A61M 25/00* (2006.01)
*B29C 48/00* (2019.01)
*B29C 48/151* (2019.01)
*B29C 63/42* (2006.01)
*B29K 105/02* (2006.01)

(52) U.S. Cl.
CPC ..... *B29C 48/0018* (2019.02); *A61M 25/0009* (2013.01); *B29C 48/022* (2019.02); *B29C 63/42* (2013.01); *B29K 2105/02* (2013.01)

(58) Field of Classification Search
CPC ............ B29K 2071/02; B29K 2096/04; B29K 2105/0085; B29K 2077/00; A61M 25/0045; A61M 25/0009; B32B 1/08; B32B 2250/24; B32B 2270/00; B32B 2274/00; B32B 2307/412; B32B 2307/702; B32B 2535/00; B32B 27/08; B32B 27/285; B32B 27/34; B32B 7/022; Y10T 428/139; Y10T 428/249921; B29C 48/0018; B29C 48/022; B29C 63/42
See application file for complete search history.

(56) References Cited

U.S. PATENT DOCUMENTS 8,740,843 B2 * 6/2014 Eaton ................. A61M 25/104
604/101.02

* cited by examiner

*Primary Examiner* — Yan Lan
(74) *Attorney, Agent, or Firm* — Jessica L. Gorczynski; Womble Bond Dickinson (US) LLP

(57) ABSTRACT

A non-crosslinked polymeric heat shrink tubing including poly(ether-block-amide) (PEBA) and methods for making such non-crosslinked polymeric heat shrink tubing is provided. The non-crosslinked PEBA heat shrink tubing disclosed herein finds application, e.g., as a processing aid and final component in the manufacture of catheters and other medical devices.

13 Claims, 17 Drawing Sheets

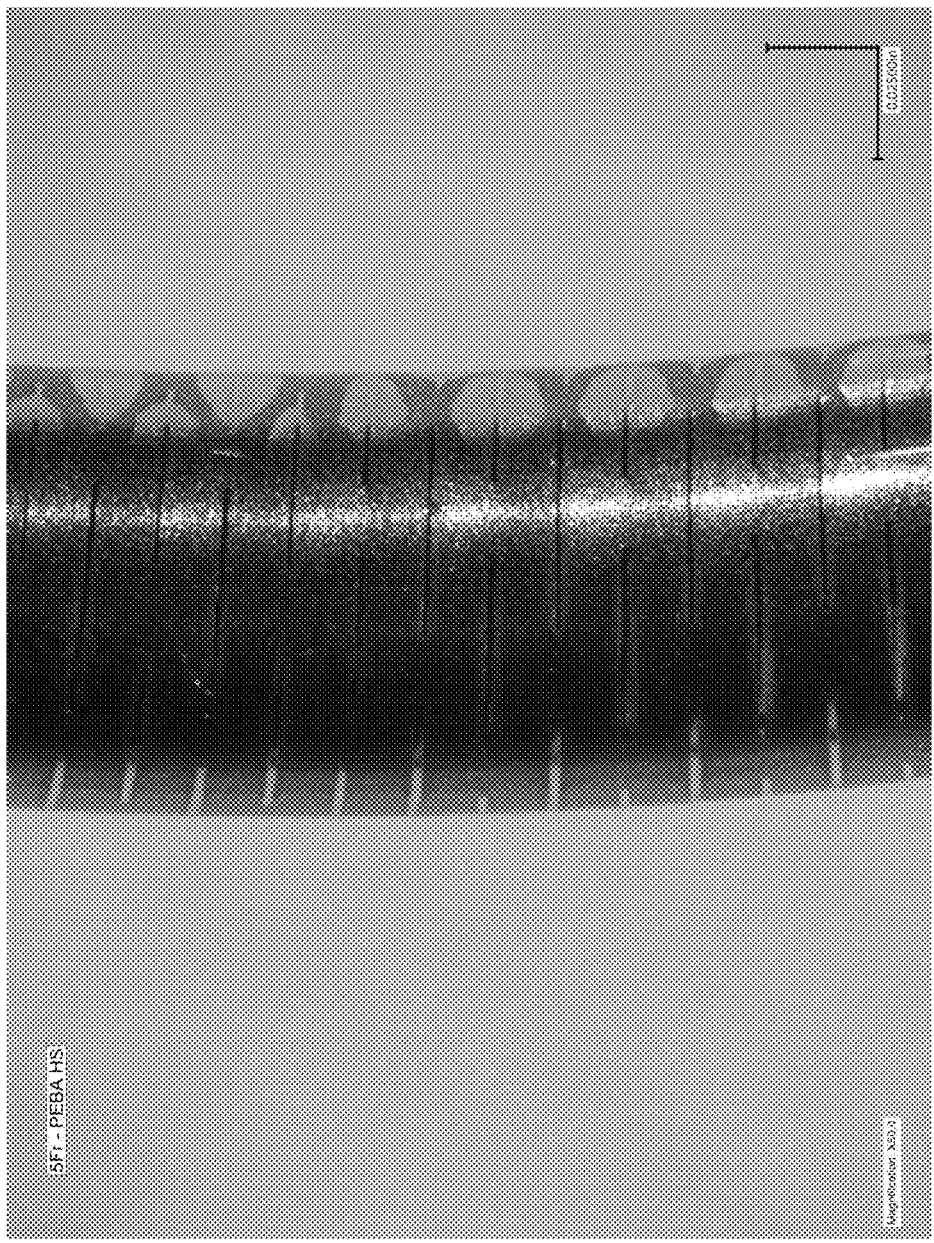
FIG. 5A (x50 magnification)

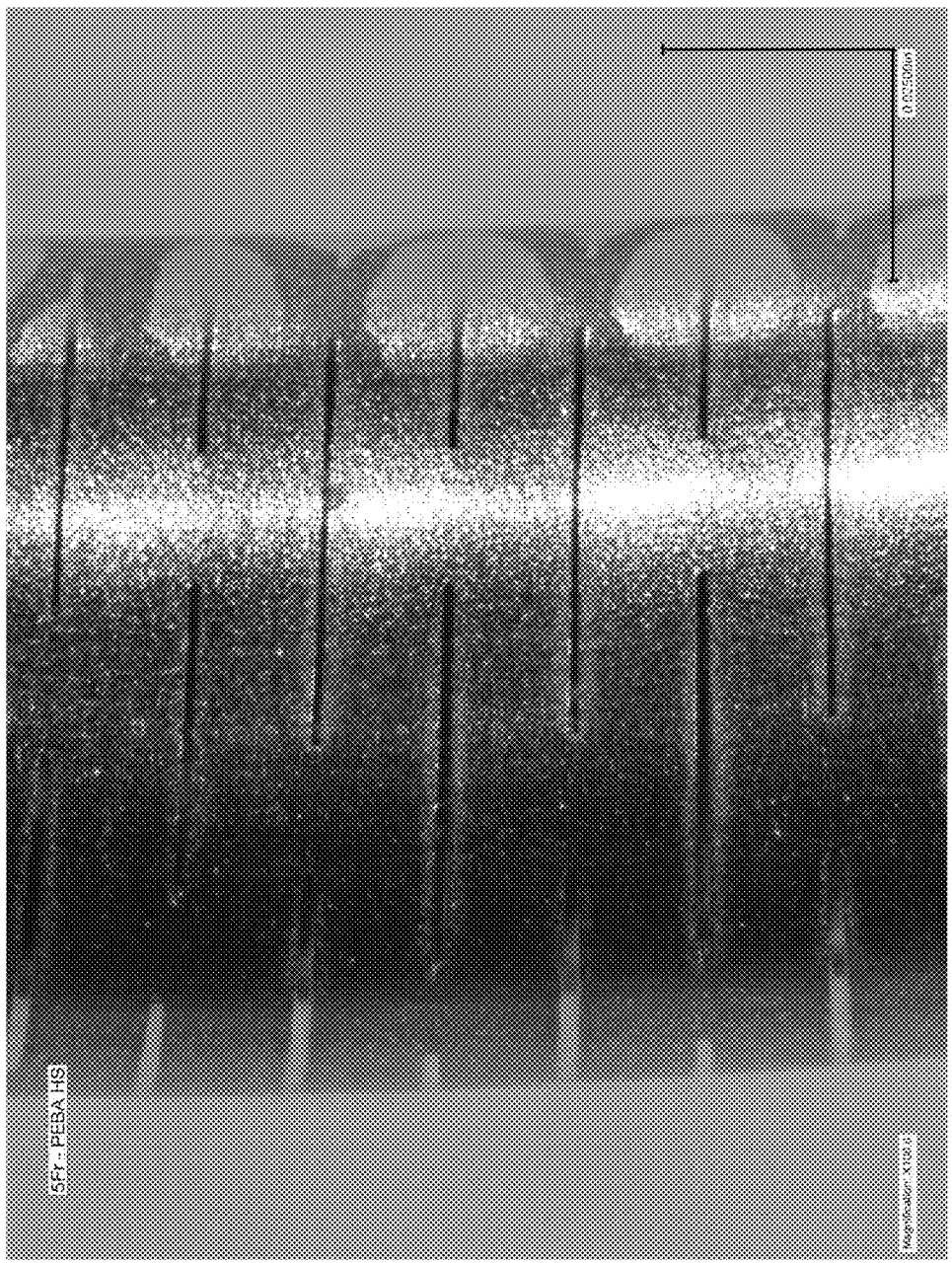
FIG. 5B (x100 magnification)

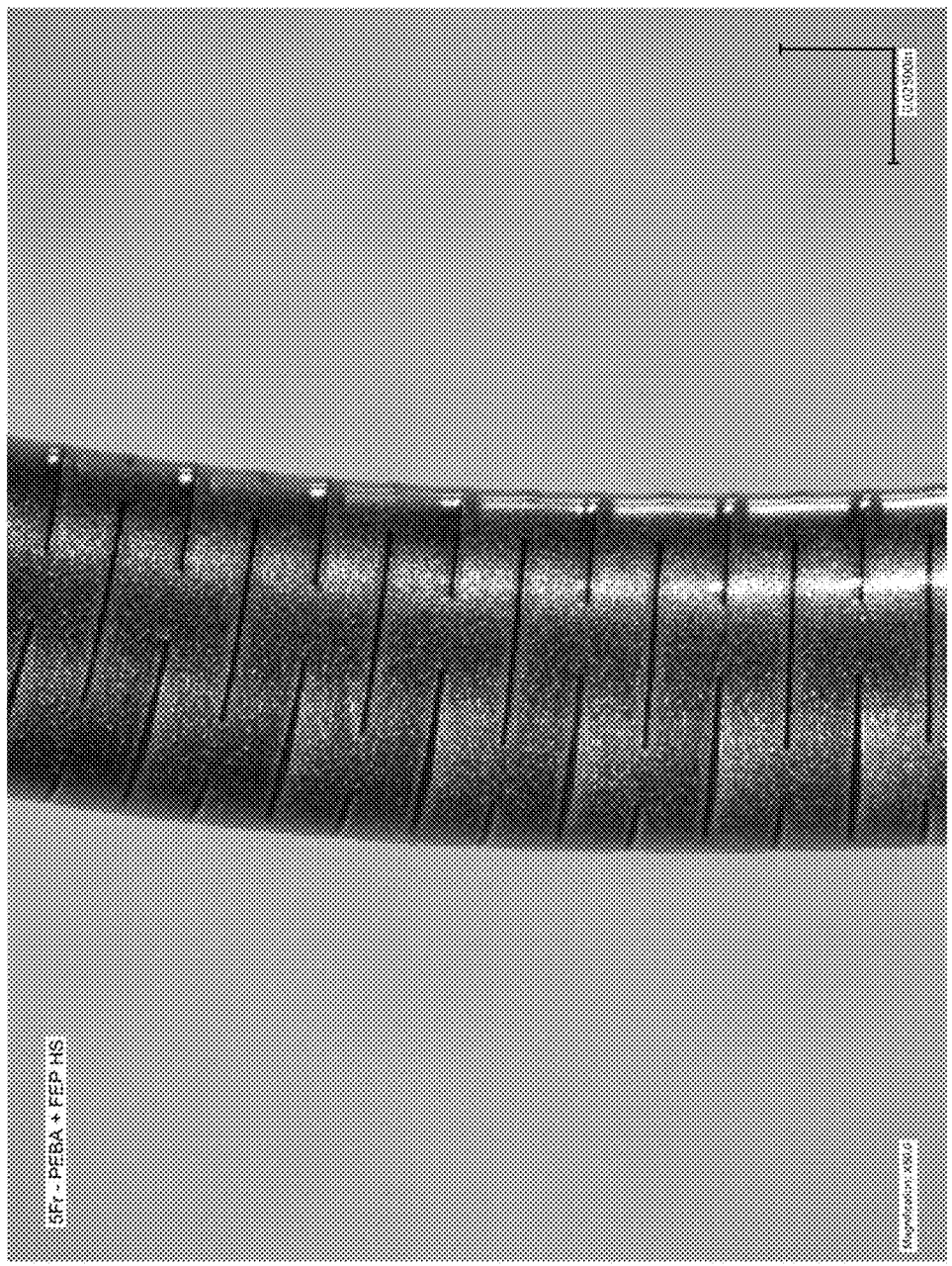
FIG. 6A (x50 magnification)

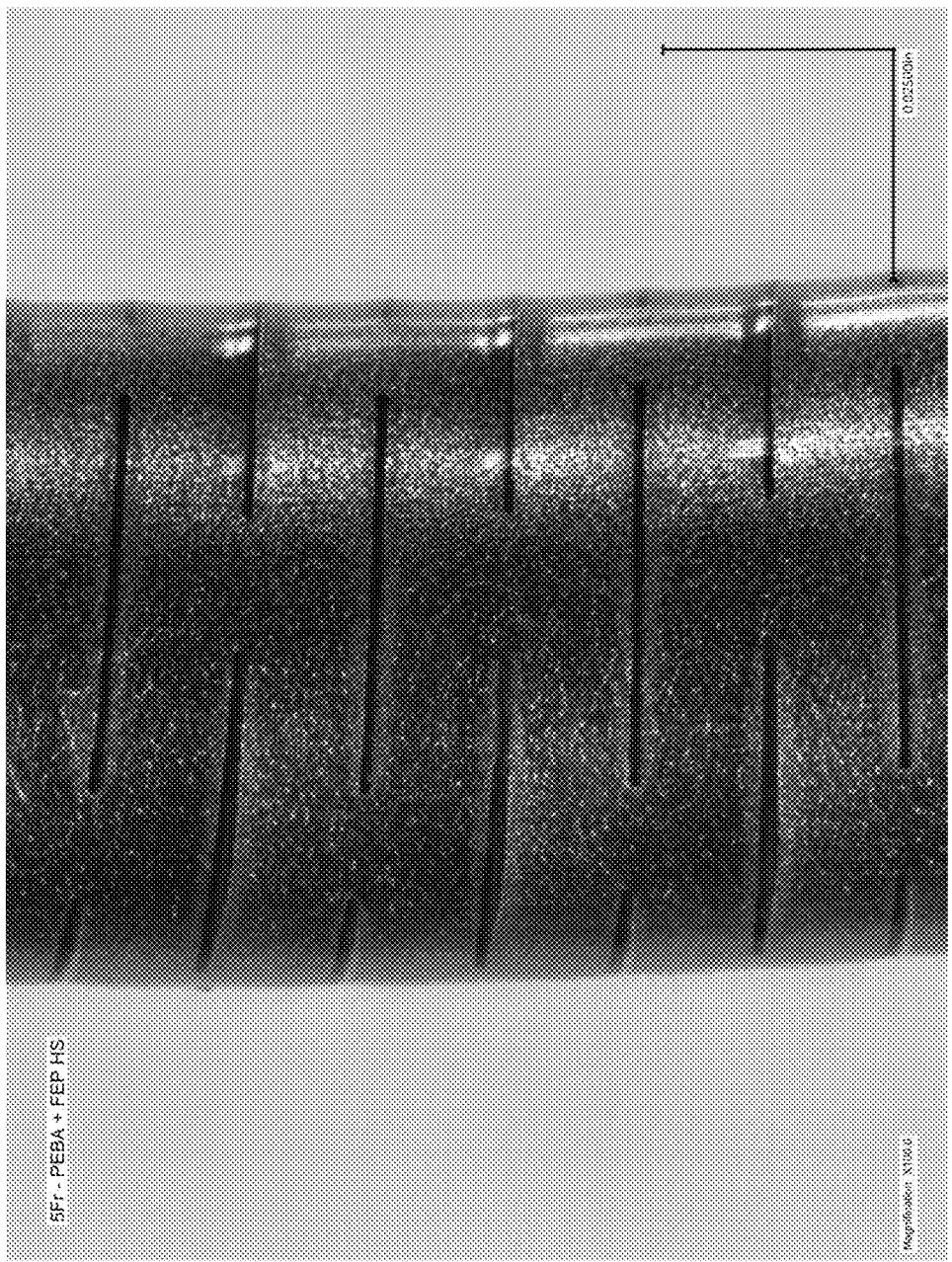
FIG. 6B (x100 magnification)

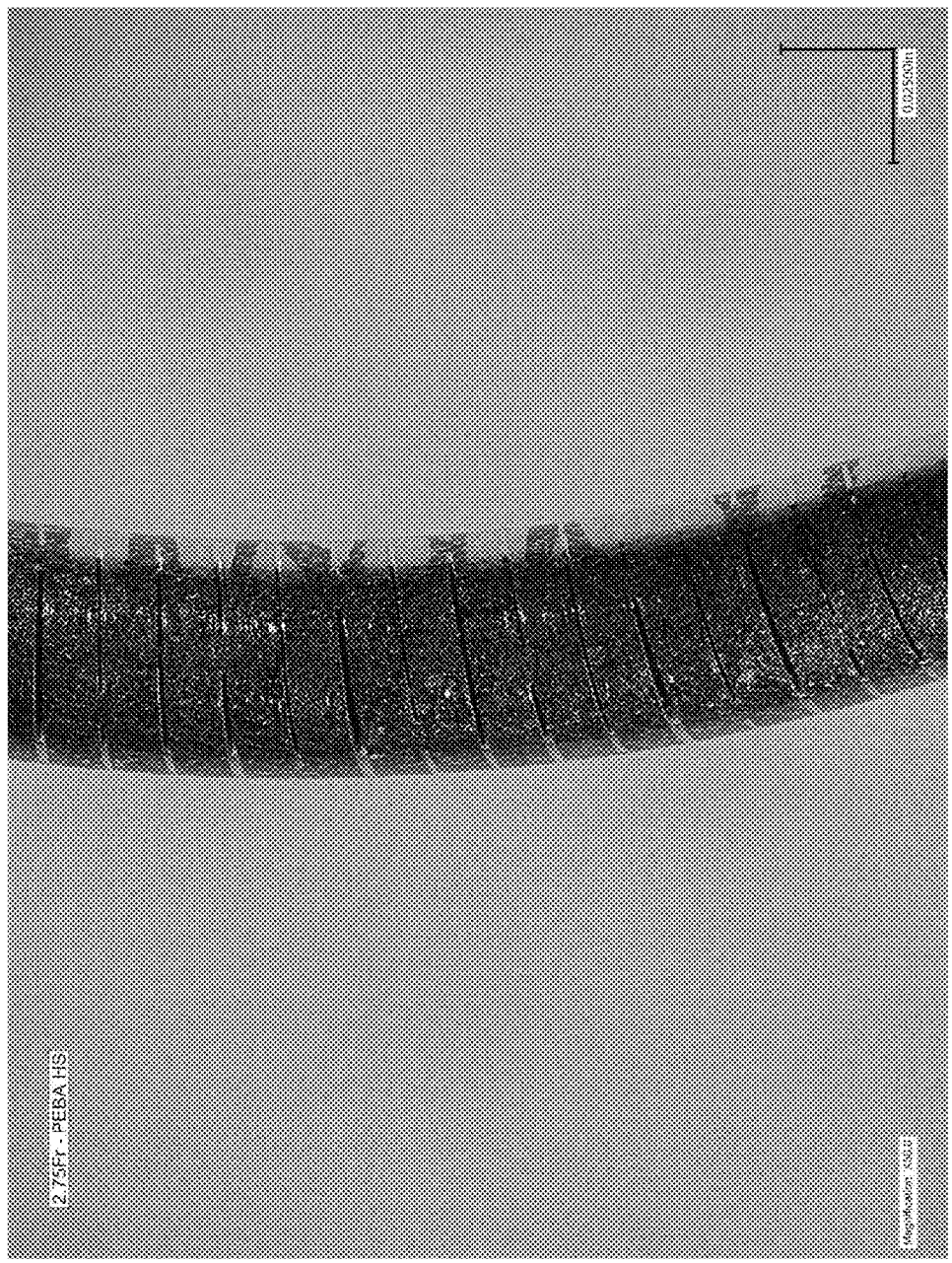
FIG. 7A (x50 magnification)

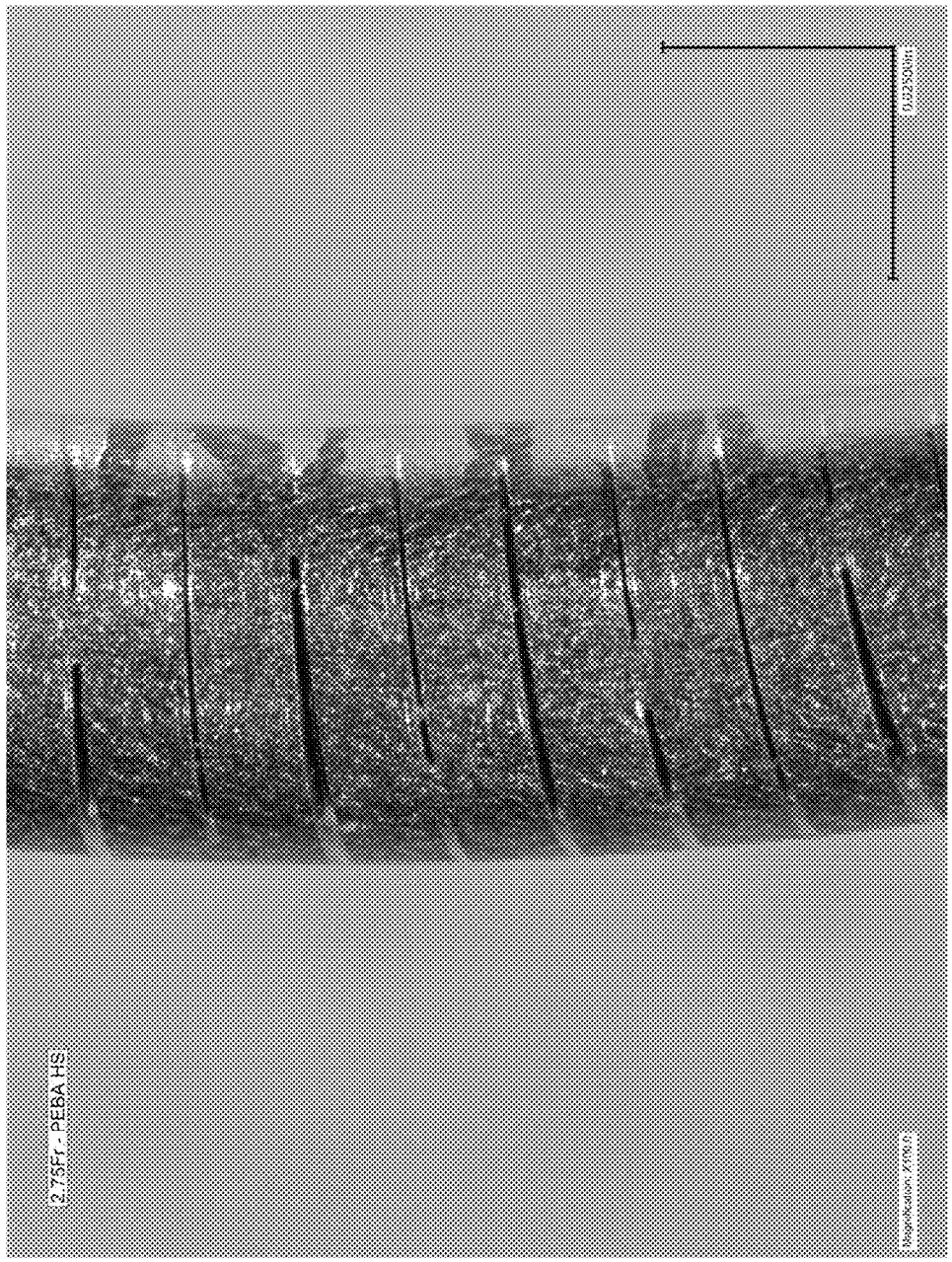
FIG. 7B (x100 magnification)

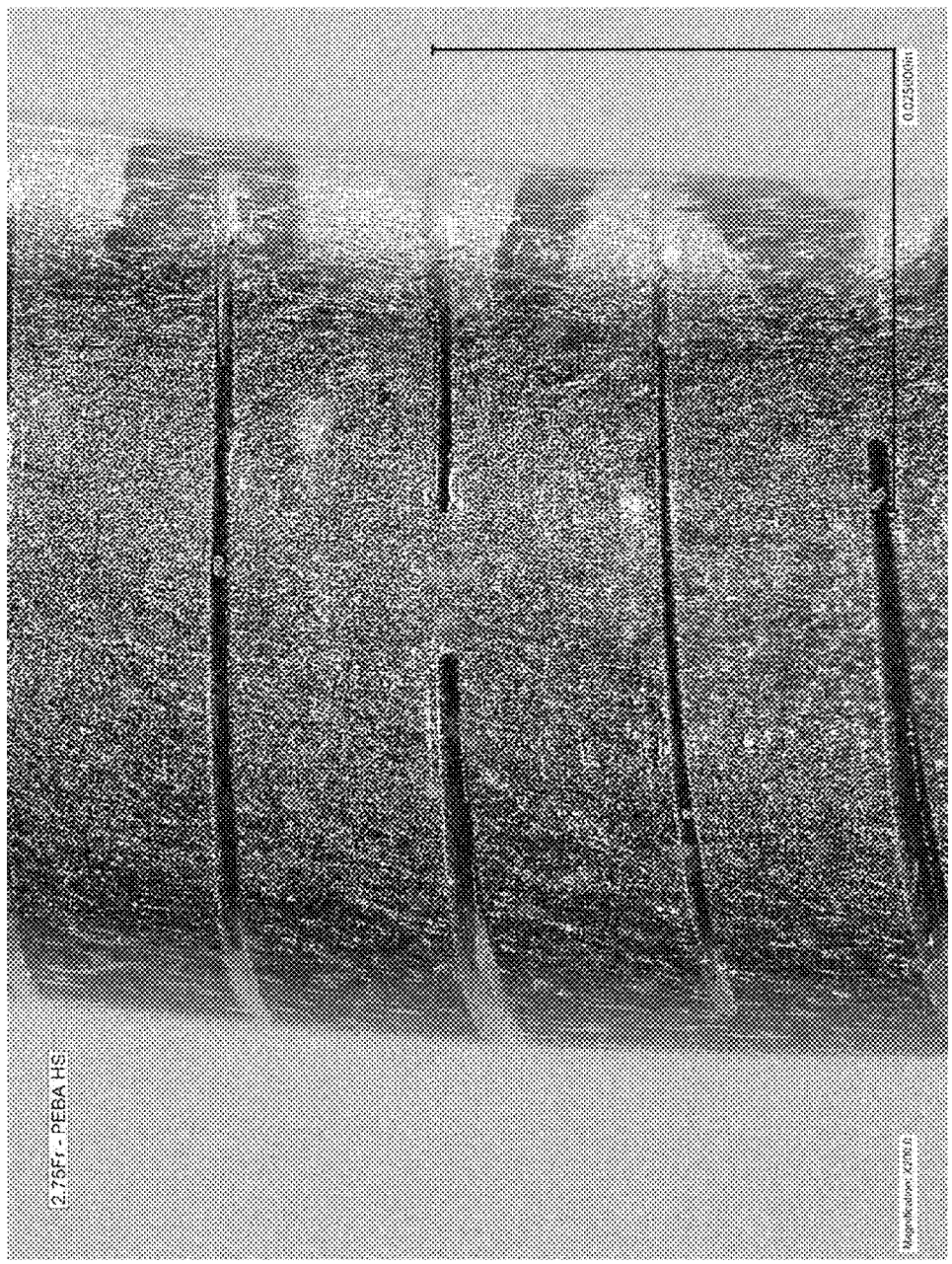
FIG. 7C (x200 magnification)

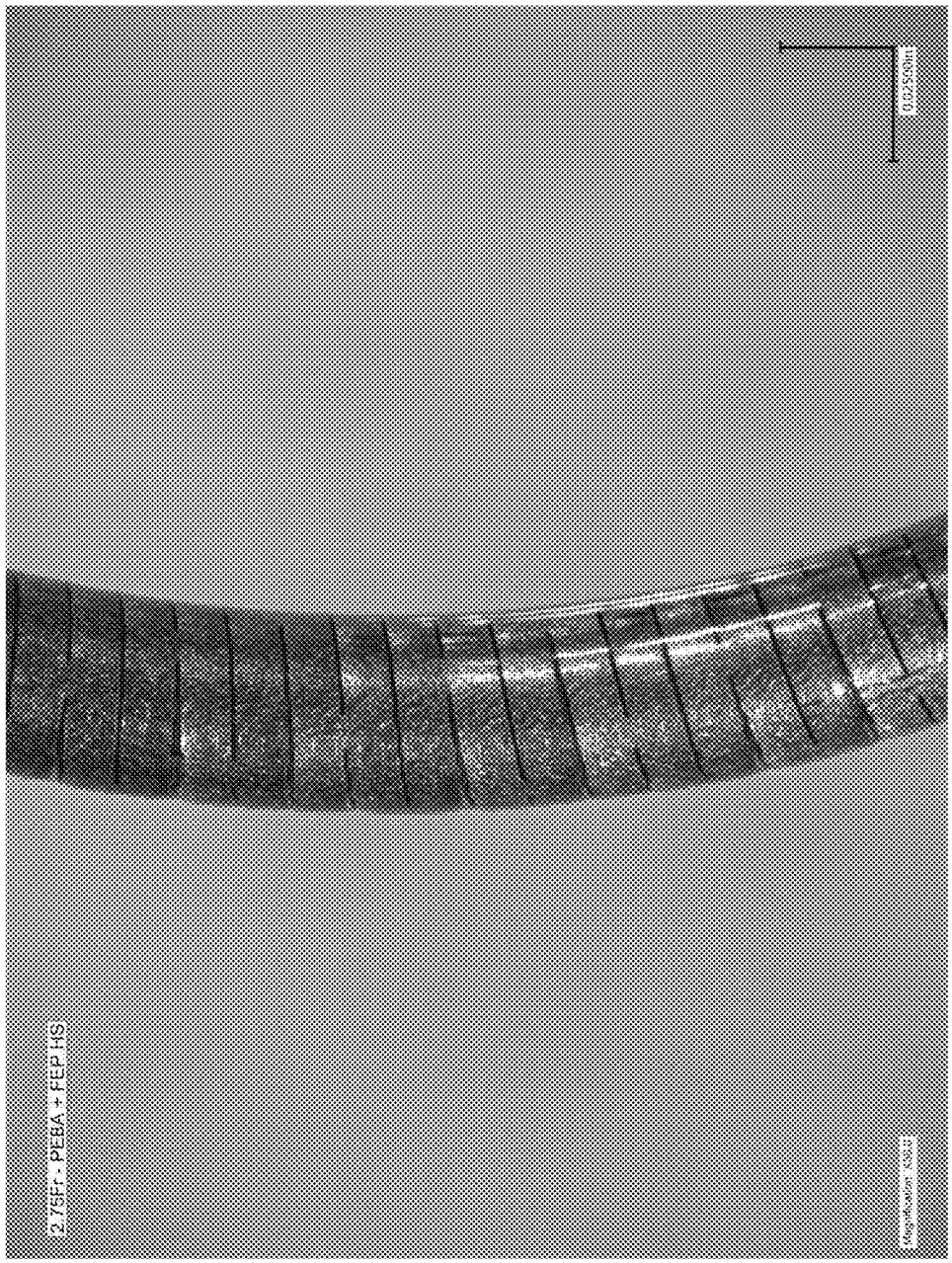
FIG. 8A (x50 magnification)

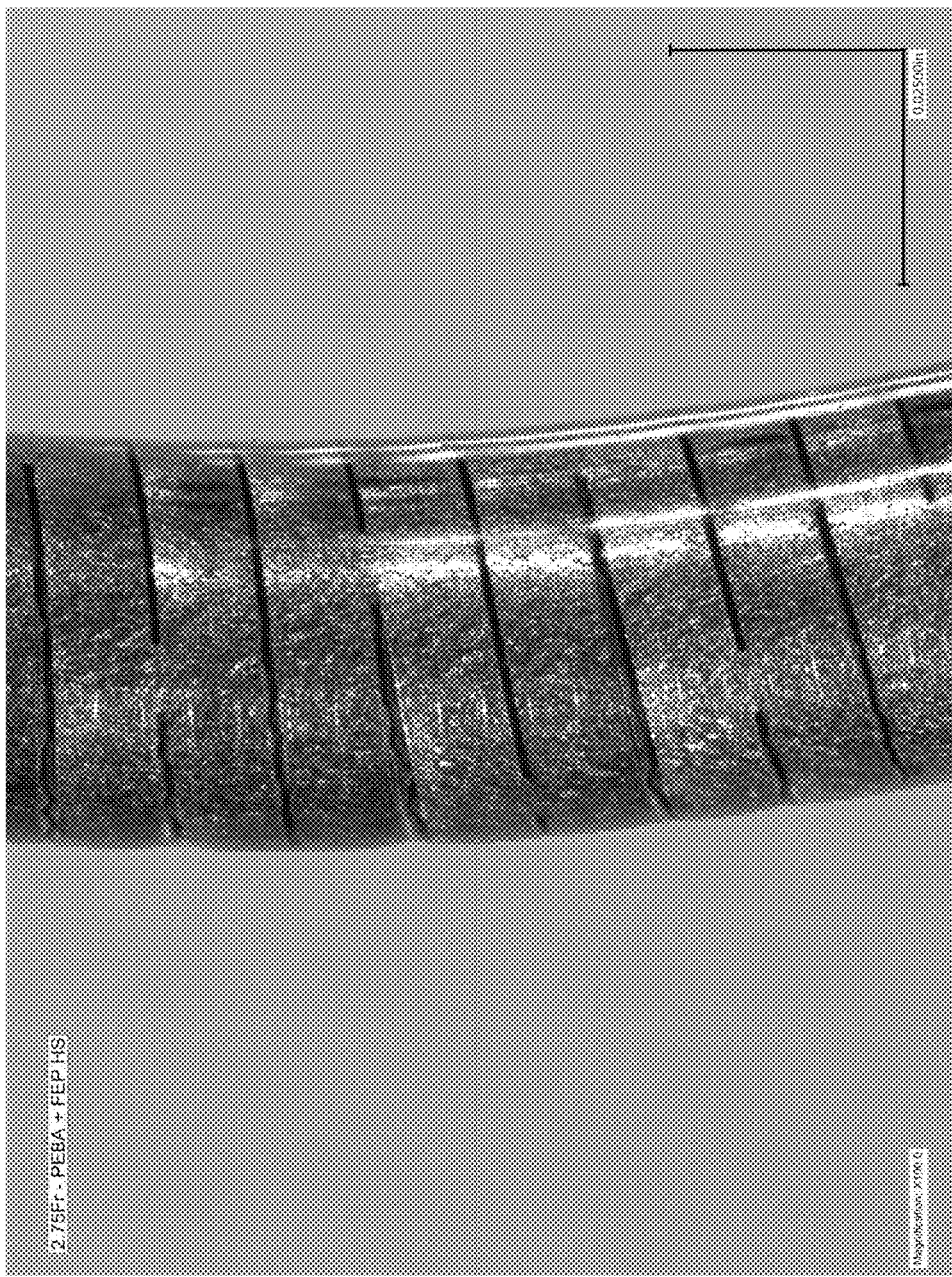
FIG. 8B (x100 magnification)

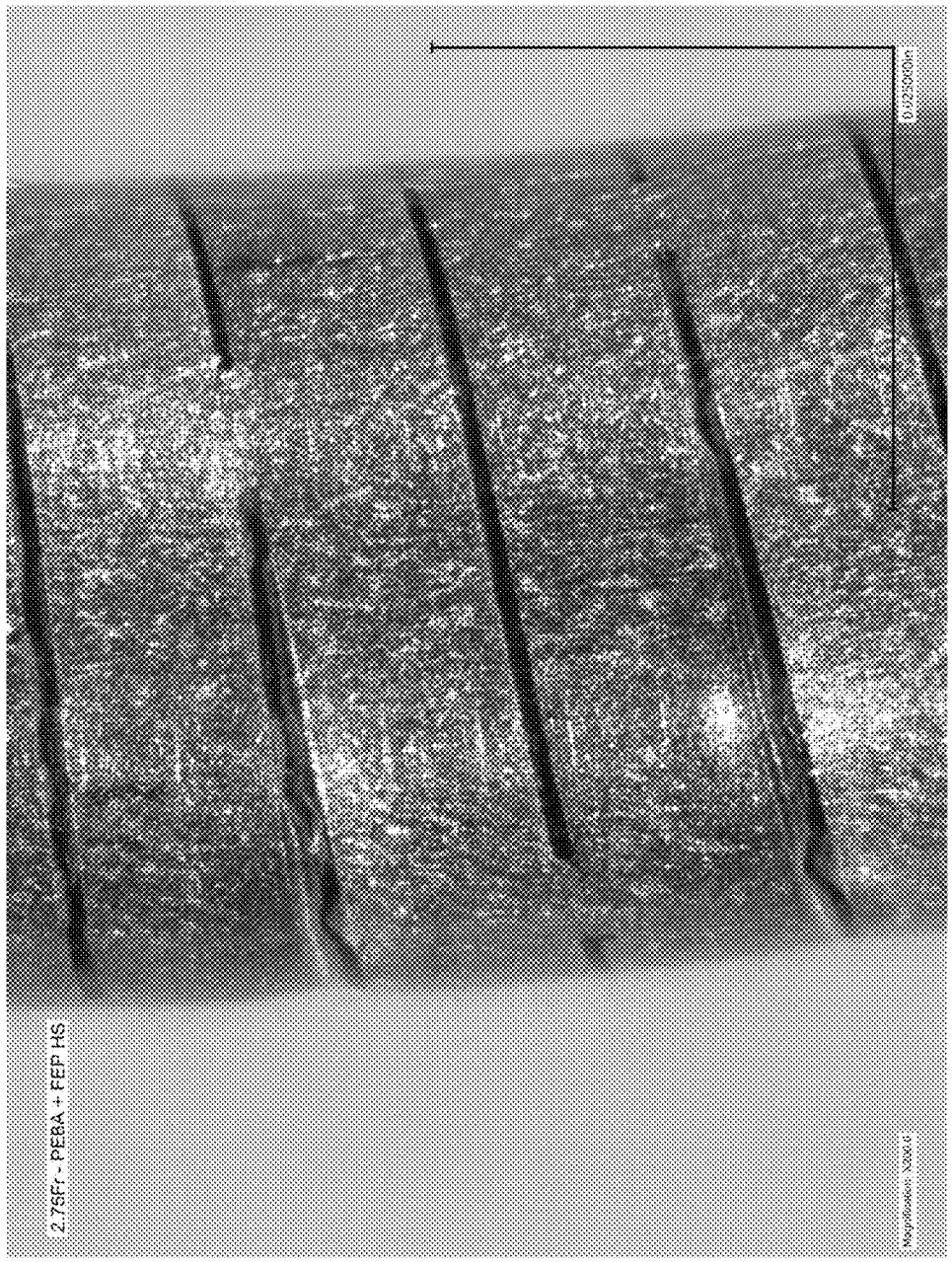
FIG. 8C (x200 magnification)

NON-CROSSLINKED HEAT SHRINK TUBING

FIELD OF THE INVENTION

The present application is directed to heat shrink polymeric tubing and methods for making such heat shrink polymeric tubing included as a component of a catheter assembly.

BACKGROUND OF THE INVENTION

Tubings manufactured from poly(ether-block-amide) (PEBA) resins are currently used as the outer sheath of many commercially available catheter shafts. Catheters are used to provide a shaft with intravenous channel through which medical devices or agents can be delivered into the body once the shaft has been inserted into position during a medical procedure. Catheters often include an inner channel lining comprising a lubricious material such as polytetrafluoroethylene (PTFE) to allow for easy insertion and retraction of medical devices therethrough. In many cases, a reinforcing component surrounds the lubricious inner channel of the catheter shaft to provide strength, pushability, and torque translation. This reinforcing component can be comprised of several different materials depending upon the target function and specifications of the finished catheter. Materials commonly used as a reinforcing component of catheter shafts include metallic or polymeric hypodermic tubing (also referred to herein as "hypotubes"), metallic wire braids or coils, liquid-crystal polymer (LCP) fiber braids, and other polymeric fibers that are braided or otherwise incorporated into the composite structure of the catheter shaft. The outer sheath, also referred to herein as a catheter jacket, serves several functions as a component of the composite catheter shaft. The jacket provides durability by covering and protecting the outer surface of the reinforcing component. The jacket also provides a barrier that defines the outer surface of the catheter, preventing leakage of fluid, agents, devices, and other therapeutics along the length of the shaft. It is desirable for the catheter jacket to have a glossy outer surface finish to provide smooth and atraumatic transmission through vasculature while in use during a medical procedure. Catheter jackets are typically comprised of polymers such as polyamide, polyurethane, polyolefin, or poly(ether-block-amide) copolymer (PEBA), which are commercially available as medical extrusion grade resins. These resins can be converted into a tubular form via melt extrusion and subsequently used in conjunction with a process aid (also often referred to as a "fusing sleeve") to provide an outer sheath for a catheter shaft.

Catheter shafts are typically manufactured by utilizing a fluorinated ethylene-propylene (FEP) heat shrink tubing as a process aid to form and bond the outer jacket to underlying components and finalize the catheter shaft build. Such heat shrink tubing has been produced commercially for several decades using various processes, for example, vacuum expansion, gas pressure forming, sequential heating/stretching and the like. Known methods for expanding heat shrink tubings are provided, for example, in the disclosures of U.S. Pat. No. 2,987,767 to Edward et al.; U.S. Pat. No. 3,412,189 to Sullivan; U.S. Pat. No. 7,625,194 to Yoshida et al.; U.S. Pat. No. 9,296,165 to Henson; U.S. Pat. No. 9,327,444 to Henson; and U.S. Pat. No. 9,440,044 to Roof et al., each of which is incorporated herein by reference in its entirety.

The conventional process for catheter manufacturing is also referred to as a "reflow process" and is well known to those skilled in the art. During the reflow process, the FEP heat shrink tubing or "fusing sleeve" is placed over a set of pre-assembled catheter shaft components (i.e., a "catheter shaft pre-assembly" or "pre-assembly") and subsequently heated to finalize the catheter shaft build. A catheter shaft pre-assembly typically comprises several components: a solid core, a thin-walled lubricious liner tube, a reinforcing component, and an outer sheath tube. Preparation of the pre-assembly can involve providing a solid core that is inserted into a thin-walled lubricious tubing (also referred to herein as a "lubricious liner" or simply "liner"). The lubricious liner typically comprises an outer-surface modified thin-walled polytetrafluoroethylene (PTFE) tube (e.g., a PTFE tube with an outer surface that has been etched, e.g., sodium etched to allow for bonding with other materials). A reinforcing component can then be applied upon the outer surface of the liner (e.g., a braid, wire coil, or hypotube structure can be applied over the outer surface of the liner). It is important to note that a reinforcing component is not always utilized in a catheter shaft build, particularly for catheter shafts that do not require a specific internal pressure resistance (i.e., burst resistance). After the reinforcing component is secured about the exterior (i.e., upon the outer surface) of the liner, an outer sheath tubing (e.g., a medical grade PEBA tube) can be applied over the reinforcing component, providing a catheter shaft pre-assembly. The pre-assembly (i.e., the solid core, the thin-walled liner tube, the reinforcing component, and the outer sheath tube) can then be inserted into an FEP heat shrink tube and heated to form and bond the outer jacket tube to the underlying components and finalize the catheter shaft. This is an effective method for manufacturing catheter shafts because the FEP heat shrink tube has a recovery (i.e., "shrink") temperature that is greater than the crystalline melting temperature of the outer sheath tubing. While heating the pre-assembly and fusing sleeve, the PEBA outer sheath tube melts and is forced by the dimensional recovery of the FEP heat shrink tube to flow radially inward and make intimate contact with the underlying components. In this way, the strong recovery force provided by the FEP heat shrink tube as it is heated (i.e., as it decreases in diameter) forces the molten PEBA tube to "reflow" within the interstices or gaps in the reinforcing material and, after cooling, a strong bond is formed between the inner surface of the outer sheath tube and the outer surface of the inner liner. Outer sheath tubes comprising polymers other than PEBA can be used in conjunction with the described reflow process. Other materials used as an outer sheath with this reflow process can comprise, for example, polyamide, polyurethane, and polyolefin. After allowing the assembly to cool, the FEP heat shrink tubing is removed and discarded. Finally, the solid core that maintains the shape of the inner lumen during reflow is removed leaving the final catheter shaft. A general schematic of a typical traditional reflow process 10 is shown in FIG. 1.

Many different methods of heat application are employed during the reflow process including, but not limited to, forced air ovens, hot boxes, induction heaters, heat guns, traversing laminators, lasers, and glow rings. For catheter shaft builds that utilize a coiled or braided reinforcing component, it is often specified for the outer jacket tube to flow into and fill all interstices/gaps between the underlying reinforcing material during the reflow process and bond to the outer surface of the inner liner to form a continuous composite structure. These types of designs often require a certain level of pressure (i.e., burst) resistance. If the interstices of the reinforcing material is insufficiently filled by the outer jacket tube during the reflow process, an air pocket or "bubble" remains embedded within the composite structure and is known as a void. Voids can negatively influence the durability and pressure resistance of the finished catheter shaft, in some cases. It is also important that the reflow process provides a strong bond between the PEBA outer jacket and the liner tube. In certain situations, delamination of the bond between the outer sheath tube and inner liner tube is unacceptable due to the potential for the thin-walled inner liner tube to kink or wrinkle in tortuous vascular pathways. This can hinder or ultimately prevent the transmission of a medical device or agents through the lumen.

Catheter shafts are often designed with variable flexibility along the length of the shaft to balance functionality and optimize performance at the proximal and distal ends. It is typically preferable for the distal end of a catheter to be soft and flexible to allow for maneuverability through vascular pathways. Conversely, it is desirable for the proximal portion of a catheter shaft to be stiffer (i.e., more rigid) than the distal end to provide pushability (i.e., columnar stiffness that aids in advancement and retraction) and predictable torque translation. This balance of functionality is commonly achieved by utilizing multiple outer sheath tubes of varying durometer hardness (i.e., PEBA tubes manufactured from different resin grades) along the length of the catheter shaft. Medical grade tubes that are comprised of, consist essentially of, or contain PEBA resins as a part of a blend, can vary significantly in durometer hardness and flexibility depending on the final composition of the tubing. For example, medical grade PEBA resins manufactured by Arkema Inc., available commercially as PEBAX MED®, vary in durometer hardness from about 25 to 74 Shore D and in flexural modulus from around 12 to 700 MPa. See e.g., Arkema's Pebax® Elastomers Brochure, which is incorporated by reference. Variable stiffness catheters are currently produced using conventional manufacturing techniques that involve FEP heat shrink tubing as a process aid. After the reinforcing component has been applied over (i.e., on the outer surface of) the inner liner, PEBA tubings across a range of durometer hardness can be sequentially slid onto and subsequently reflowed over the reinforcing component to provide the desired flexibility to each portion of the catheter shaft, forming a multi-durometer catheter shaft. This provides catheter manufacturers with the ability to alter the characteristics of the completed shaft for a specific application by varying the length and composition of the outer jacket. To finalize the multi-durometer catheter build, the prepared components are inserted into the FEP fusing sleeve and subsequently heated to melt and reflow the outer sheath tubings to provide a catheter with sections of varying flexibility (i.e., durometer hardness). It is important to note that the circumferential mechanical force provided by the FEP fusing sleeve (i.e., as it "shrinks" at a temperature above the melting point of the underlying outer sheath tubings) forces coalescence at the interface of the outer sheath tubings to provide smooth transitions between the sections.

Another approach for achieving variable flexibility along the length of a catheter shaft involves varying the stiffness of the reinforcing component. This can be achieved through varying braid materials and patterns along the length but is more fully customizable through the use of laser-cut hypotubes. These hypotubes can comprise metallic or polymeric materials and typically have a cut pattern that changes or transitions along the length. Many commercially available laser-cut hypotubes involve a cut pattern that is helical and either continuous or interrupted along the length. The helical laser-cut pattern can continuously or abruptly transition in terms of cut pitch, cut width, cut spacing, and other characteristics along the length of the shaft. A wide variety of hypotubes are known in the art and can be used according to the present disclosure. For catheter shafts involving laser cut hypotubes as the reinforcing component, it is undesirable for the outer jacket to flow within the laser-cut gaps as this will alter the variable flexibility that is engineered into the cut pattern design. Using conventional catheter manufacturing techniques involving FEP heat shrink for these types of catheter shafts poses a great challenge for medical device manufacturers and designers.

The use of FEP heat shrink tubing adds significant material costs to the catheter manufacturing process. Development and optimization of the dimensional and recovery characteristics of the FEP fusing sleeve must be optimized for a particular catheter shaft build, most often through a third-party supplier, which can be very costly and time consuming. Some of these optimizations include adjustments to sizing, required recovery ratio, and recovery conditions that provides void elimination and a good bond between the jacket and inner liner. The labor and tooling required to remove the FEP heat shrink tubing also contributes to increased operating costs. There is also potential for the finished catheter shaft to be damaged and scrapped as a result of having to remove the FEP fusing sleeve after the reflow process. Moreover, the scrap FEP material generated is inconsistent with the goals of a circular economy.

SUMMARY OF THE INVENTION

The present disclosure relates to heat shrinkable polymeric tubes comprising one or more polymers that are not cross-linked. In some embodiments, the disclosure relates to heat shrinkable ("heat shrink") tubes comprising poly(ether-block-amide) copolymer (PEBA), wherein the PEBA is not crosslinked. Typically, such heat shrink tubes are in the form of extruded and expanded tubes. Surprisingly, it has been found that certain such extruded tubes can be expanded to form heat shrink tubes without a crosslinking step. Such heat shrink tubes can be subsequently employed during catheter shaft assembly processes as an outer jacket for catheter shafts without the need for expensive single-use manufacturing aids such as FEP heat shrink tubes. With propitious conditions of expansion, recovery ratio, and time/temperature profile for the recovery process, a satisfactory catheter shaft can be manufactured using a tube comprising non-crosslinked PEBA, which does not require removal of any single-use manufacturing aid prior to use. Several catheter shaft configurations comprising a variety of components can be assembled utilizing such a heat shrink tube as an outer jacket under conditions to be explained more fully hereafter.

The invention includes, without limitation, the following embodiments.

Embodiment 1: A heat shrink tubing comprising non-crosslinked PEBA, wherein the heat shrink tubing has a recovery ratio (RR) greater than about 1.05:1 and/or is reducible in internal diameter (ID) by about 4.8%.

Embodiment 2: The heat shrink tubing of Embodiment 1, consisting essentially of the non-crosslinked PEBA.

Embodiment 3: The heat shrink tubing of any of Embodiments 1-2, wherein the RR is greater than about 1.10:1 and/or is reducible in ID by about 9.1%.

Embodiment 4: The heat shrink tubing of any of Embodiments 1-3, wherein the RR is greater than about 1.2:1 and/or is reducible in ID by about 16.7%.

Embodiment 5: The heat shrink tubing of any of Embodiments 1-4, wherein the RR is greater than about 1.3:1 and/or reducible in ID by about 23.1%.

Embodiment 6: The heat shrink tubing of any of Embodiments 1-5, wherein the RR is greater than about 1.4:1 and/or reducible in ID by about 28.6%.

Embodiment 7: The heat shrink tubing of any of Embodiments 1-6, wherein the RR is greater than about 1.5:1 and/or reducible in ID by about 33.3%.

Embodiment 8: The heat shrink tubing of any of Embodiments 1-7, wherein the RR is greater than about 1.6:1 and/or reducible in ID by about 37.5%.

Embodiment 9: The heat shrink tubing of any of Embodiments 1-8, wherein a durometer hardness measurement according to ASTM D2240 conducted on a flat specimen fabricated by melt pressing the heat shrink tubing in expanded form is about 20 to 80 Shore D.

Embodiment 10: The heat shrink tubing of any of Embodiments 1-9, recovered over a PTFE liner, e.g., a surface-modified PTFE liner.

Embodiment 11: The heat shrink tubing of any of Embodiments 1-9, recovered over a laser-cut hypotube.

Embodiment 12: The heat shrink tubing of any of Embodiments 10 or 11, wherein the heat shrink tubing exhibits a cohesive failure mode when peeled from the underlying PTFE liner or laser-cut hypotube.

Embodiment 13: The heat shrink tubing of any of Embodiments 10-12, wherein the outer surface is modified after recovery by passing the tubing through a heated die, e.g., to modify the smoothness of the surface (providing a smooth outer surface or a textured/engineered surface) to alter or enhance the sliding properties of the material.

Embodiment 14: The heat shrink tubing of any of Embodiments 1-13, further comprising a liquid or polymeric coating on an outer surface of the tubing that enhances the lubricity or chemical resistance of the tubing.

Embodiment 15: The heat shrink tubing of Embodiment 14, wherein the liquid or polymeric coating is hydrophobic.

Embodiment 16: A catheter comprising the non-crosslinked heat shrink tubing of any of Embodiments 1-9.

Embodiment 17: The catheter of Embodiment 16, selected from the group consisting of a guide catheter, microcatheter, balloon catheter, and steerable delivery catheter.

Embodiment 18: A method of making the heat shrink tubing of any of Embodiments 1-15, comprising: extruding a PEBA resin into a tubular form; and expanding the tubular form.

Embodiment 19: A method of assembling a catheter, comprising: providing a catheter pre-assembly comprising a solid core, a liner comprising PTFE, a reinforcing component, and the heat shrink tubing of any of Embodiments 1-9; and heating the catheter pre-assembly, wherein the method does not involve a step of applying a further heat shrink tubing over the heat shrink tubing.

Embodiment 20: A construct, comprising: a first tube selected from a liner comprising PTFE and a laser-cut hypotube; and a second tube disposed over the first tube, wherein the second tube is the heat shrink tubing of any of Embodiments 1-15.

Embodiment 21: A construct, comprising: a first tube selected from a liner comprising PTFE and a laser-cut hypotube; and a second tube disposed over the first tube, wherein the second tube comprises non-crosslinked PEBA.

Embodiment 22: The construct of Embodiment 21, wherein the second tube is a heat shrink tube in an expanded form.

Embodiment 23: The construct of Embodiment 21, wherein the second tube is a heat shrink tube in recovered form.

Embodiment 24: The construct of any of Embodiments 20-23, wherein the second tube consists essentially of non-crosslinked PEBA.

Embodiment 25: The construct of any of Embodiments 20-24, wherein the first tube is a liner comprising PTFE and wherein the liner has an etched outer surface.

Embodiment 26: The construct of any of Embodiments 20-25, wherein the first tube is a liner comprising PTFE and the construct further comprises a reinforcing component between the first tube and the second tube.

Embodiment 27: The construct of Embodiment 26, wherein the reinforcing component is selected from the group consisting of a braid, a coil, or a hypotube.

Embodiment 28: The construct of any of Embodiments 20-27, further comprising a tie layer.

Embodiment 29: The construct of any of Embodiments 20-28, wherein the construct exhibits a cohesive failure mode when the first tube is peeled off of the second tube.

It will be apparent to those skilled in the art that other embodiments of the invention are possible and that the examples presented here are not intended to be exhaustive. These and other features, aspects, and advantages of the present disclosure will be apparent from a reading of the following detailed description together with the accompanying drawings, which are briefly described below. The present disclosure includes any combination of two, three, four, or more features or elements set forth in this disclosure or recited in any one or more of the claims, regardless of whether such features or elements are expressly combined or otherwise recited in a specific embodiment description or claim herein. This disclosure is intended to be read holistically such that any separable features or elements of the disclosure, in any of its aspects and embodiments, should be viewed as intended to be combinable, unless the context of the disclosure clearly dictates otherwise.

BRIEF DESCRIPTION OF THE DRAWINGS

In order to provide an understanding of embodiments of the invention, reference is made to the appended drawings, which are not necessarily drawn to scale, and in which reference numerals refer to components of exemplary embodiments of the invention. The drawings are exemplary only, and should not be construed as limiting the invention.

FIGS. 5A and 5B are microscopic images captured during the examination of Example 10—a 5 French stainless-steel laser-cut hypotube that was covered using the recovery method 20 with the non-crosslinked PEBA heat shrink tube of Example 9. FIG. 5A was obtained at a magnification of ×50 and FIG. 5B was obtained at a magnification of ×100;

FIGS. 6A and 6B are microscopic images captured during the examination of Comparative Example 6—a 5 French stainless-steel laser-cut hypotube that was covered using the traditional reflow method 10 with the non-crosslinked PEBA heat shrink tube of Example 9 and an appropriately sized FEP heat shrink fusing sleeve. The FEP heat shrink fusing sleeve was skived from the build before microscopic examination. FIG. 6A was obtained at a magnification of ×50 and FIG. 6B was obtained at a magnification of ×100;

FIGS. 7A, 7B, and 7C are microscopic images captured during the examination of Example 11—a 2.75 French stainless-steel laser-cut hypotube that was covered using the recovery method 20 with the non-crosslinked PEBA heat shrink tube of Example 8. FIG. 7A was obtained at a magnification of ×50, FIG. 7B was obtained at a magnification of ×100, and FIG. 7C was obtained at a magnification of ×200;

FIGS. 8A, 8B, and 8C are microscopic images captured during the examination of Comparative Example 7—a 2.75 French stainless-steel laser-cut hypotube that was covered using the traditional reflow method 10 with the non-crosslinked PEBA heat shrink tube of Example 8 and an appropriately sized FEP heat shrink fusing sleeve. The FEP heat shrink fusing sleeve was skived from the build before microscopic examination. FIG. 8A was obtained at a magnification of ×50, FIG. 8B was obtained at a magnification of ×100, and FIG. 8C was obtained at a magnification of ×200;

DETAILED DESCRIPTION

Figure 1A:
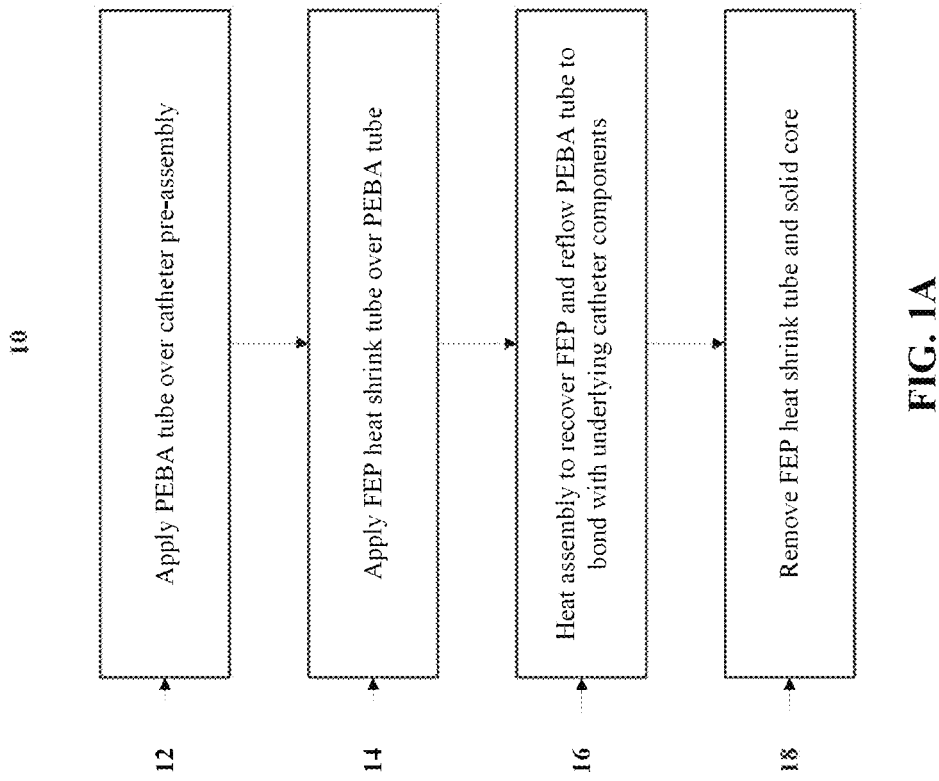
FIGS. 1A and 1B are general schematics for typical reflow catheter shaft manufacturing method 10 (FIG. 1A) and recovery catheter shaft manufacturing method 20 of one embodiment of the present disclosure (FIG. 1B)

The present invention will now be described more fully hereinafter with reference to the accompanying figures, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The present disclosure provides heat shrink tubes with unique properties and unique combinations of properties, as will be outlined further herein. Generally, a heat shrink tubing is a shrinkable tubing prepared via expansion of a polymeric ("input") tubing (e.g., an extruded tubing) to give the heat shrink tubing (also referred to herein as an "expanded" form). Upon heating, the heat shrink tubing "shrinks" to a size that is equivalent to (or close to) its original/input size, commonly referred to as its "recovered" size. The composition and overall size of a heat shrink tubing according to the present disclosure can vary widely and is not particularly limited. A heat shrink tubing can be defined, e.g., by measurable properties such as its inner diameter ("ID") either after expansion (also referred to herein as "expanded inner diameter" ($ID_e$)) or after recovery (also referred to herein as "recovered inner diameter" ($ID_r$)), its length (L), its change in length upon recovery (i.e., its percent change in length upon recovery, $\Delta L$), its average wall thickness, its wall thickness concentricity (also referred to herein as percent concentricity or simply as concentricity), its expansion ratio (ER), its recovery ratio (RR), and its percent change in inner diameter upon recovery ($\Delta ID$). Such properties can be defined using the following equations:

$$\text{Expansion ratio} = ER = \frac{ID_e}{ID_o}$$

$$\text{Recovery ratio} = RR = \frac{ID_e}{ID_r}$$

$$\% \text{ Change in Length} = \Delta L = \frac{L_r - L_e}{L_e}(100)$$

$$\% \text{ Change of Inner Diameter} = \Delta ID = \frac{ID_e - ID_r}{ID_e}(100)$$

$$\% \text{ Concentricity} = \frac{wt_{min}}{wt_{max}}(100)$$

In these equations, $L_e$ and $L_r$ are the length of the heat shrink tubing (in expanded form) and the length of the "recovered" (i.e., heat-shrunk) tubing, respectively. $ID_o$ refers to the original internal diameter (ID) of the input tube (i.e., the tube before it is expanded and then subsequently "shrunk"); $ID_e$ refers to the internal diameter (ID) of the expanded heat shrink tubing; and $ID_r$ refers to the internal diameter (ID) of the recovered (heat shrunk) tube. Values needed for determination of percent concentricity are the minimum wall thickness and the maximum wall thickness of the tubular walls, defined as $wt_{min}$ and $wt_{max}$, respectively. RR, ΔL, and ΔID can be evaluated under any recovery conditions (i.e., time, temperature, and method of heat application), though the time and temperature at which an expanded tube is recovered must be specified as this can influence the observed extent of recovery (i.e., an expanded tube that is exposed to a lower temperature and/or for a shorter time may not recover to its full capability). Percent concentricity can be evaluated in the expanded or recovered state. Concentricity is a measure of wall thickness uniformity, and the concentricity value can influence performance in certain applications in both states. As used herein, the above parameters were calculated as follows.

The percent change in length (ΔL), also referred to herein as longitudinal change, is determined in the following manner. Prior to placing the heat shrink tubing into the oven for unrestricted recovery, the expanded tubing is cut to a length of 2.5 inches using a verified ruler. The 2.5-inch specimen length is carefully cut from the heat shrink tubing so as to ensure there are no burs or other deformities present, and that they are perpendicular to the longitudinal axis of the tubing. After the unrestricted recovery process at a specified temperature, the tubing length is re-measured using a verified ruler to the nearest 1/32nd of an inch to determine the amount of shrinkage or growth that has occurred during the process. For example, the expanded length is subtracted from the recovered length and divided by the expanded length, then this quantity is multiplied by 100 to give the overall percent change in length (ΔL) resulting from recovery. Typically, ΔL is measured to be in the range of about +/−10% (i.e., the length changes by less than about 10% upon recovery). In some embodiments, the longitudinal change is measured to be in the range of about +/−9%, about +/−5%, or about +/−2%. In certain embodiments, longitudinal change has been averaged at 2% or less.

The recovery ratio (RR), percent change in inner diameter (ΔID), and percent concentricity is determined in the following manner. Three 2.5-inch-long specimens are cut from the expanded tubing and their expanded ID and wall thickness is measured using verified measurement tools. Multiple wall thickness measurements must be taken to accurately determine the percent concentricity (i.e., the wall thickness uniformity) of the tubular walls. The minimum wall thickness measurement taken on the expanded tube is divided by the maximum wall thickness measurement taken on the expanded tube, and then multiplied by 100 to give the percent concentricity of the expanded tube. The specimens are then placed into an oven set at a specified temperature for approximately 10 minutes. After exposing each heat shrink tubing specimen to a specified recovery temperature for 10 minutes, it is removed from the oven and allowed to cool to ambient temperature. This subjects the expanded heat shrink tubing to an unrestricted recovery process. After cooling to ambient temperature, the recovered ID and wall thickness is measured using verified measurement tools. The expanded tubing ID is divided by the recovered tubing ID to calculate the recovery ratio (RR) of the heat shrink tube under the specified recovery conditions (i.e., recovery temperature and time). Subsequently, the percent inner diameter change of the heat shrink tubing is calculated by subtracting the recovered tubing ID from the expanded tubing ID and dividing by the expanded tubing ID, then multiplying this quantity by 100 to give the overall percent change in inner diameter (ΔID). The minimum wall thickness measurement taken on the recovered tube is divided by the maximum wall thickness measurement taken on the recovered tube, and then multiplied by 100 to give the percent concentricity of the recovered tube.

In some embodiments, the disclosed non-crosslinked heat shrink tubes comprise, consist essentially of, or consist of one or more polymers such as polyamides, polyethers, polyesters, poly(ether-block-amides); or a copolymer, blend, or derivative of any two or more of the foregoing. Exemplary polymers according to the present disclosure include, but are not limited to, a poly(ether-block-amide) (PEBA) (i.e., a block copolymer comprised of a polyamide segment (e.g., polyamide 6 (PA6), or polyamide 11 (PA11), or polyamide 12 (PA12)), a polyether segment (e.g., polyoxymethylene (POM), or polyethylene glycol (PEG), or polypropylene glycol (PPG), or polytetramethylene glycol (PTMG)), and may include a polyester segment in some grades (e.g., poly(ethylene adipate) (PEA)).

In certain specific embodiments, non-crosslinked heat shrink tubes comprising PEBA are provided. When referring to the composition of a particular PEBA resin grade, the polyamide segment can be referred to as the "hard segment" or "hard phase", the polyether segment can be referred to as the "soft segment" or "soft phase", and the polyester segment (if present in low composition in particular grades of PEBA resin) acts as a chain extender. The ratio of the polyamide, polyether, and polyester segments of the PEBA in the heat shrink tube can vary greatly without departing from the present disclosure Different composition ratios of the polyamide hard segment to polyether soft segment (in addition to a polyester chain extender in some resin grades) influences the physical properties of the supplied resin; and ultimately the final physical properties of the non-crosslinked PEBA heat shrink tubes of the present invention. Different composition ratios allow for non-crosslinked PEBA heat shrink tubes of varying flexibility (i.e., durometer hardness) to be produced.

In various embodiments, the heat shrink tubings disclosed herein are prepared from one or more poly(ether-block-amide) (PEBA) resins. "Resin" as used herein refers to a material consisting essentially of a given type of polymer (e.g., a copolymer) or two or more polymers/copolymers. Resins are typically provided in solid form (e.g., as solid pellets), although they are not limited thereto (with other forms including, but not limited to, powders, pastes, granules, dispersions, solutions, gels, and the like). In some embodiments, the heat shrink tubings disclosed herein may be prepared from a resin comprising, consisting of, or consisting essentially of a PEBA resin in one or more of the forms noted herein. In some cases, a "resin" as used herein may contain one or more additional components as additives and/or one or more additional components can be added thereto (e.g., such as a lubricant, colorant, filler, and the like). In other embodiments, one or more additional components (in granular, powder, or pellet form or in the form of a gel or liquid) can be included with the PEBA resin and extruded therewith. As such, the heat shrink tube ultimately produced can comprise, in some embodiments, one or more such additional component(s)).

In certain embodiments, heat shrink tubes of the present disclosure are prepared using a PEBA resin, and thus in some embodiments, can consist of PEBA, can consist essentially of PEBA, or can comprise PEBA. Typically, PEBA resins can be provided in a variety of different forms, for example, such as in the forms of solid pellets, powders, granules, dispersions, solutions, gels, and the like. In certain embodiments, PEBA heat shrink tubes may be prepared using medical extrusion grade PEBA resin pellets. The type of PEBA resin that is utilized in certain embodiments can vary and may include PEBA medical extrusion grade pellets of different compositions (i.e., different durometer hardness), either as a single PEBA copolymer resin grade, as a blend of two or more PEBA copolymer resin grades, or as a blend that includes a PEBA copolymer resin grade. The PEBA resins utilized in certain embodiments may also be blended or compounded with other polymeric components (e.g., such as polytetrafluoroethylene (PTFE)) to tailor the final properties of the resulting non-crosslinked heat shrink tube for a particular application. Exemplary medical extrusion grade PEBA resins suitable for use according to the present disclosure are commercially available as PEBAX® 7433 SA 01 MED, PEBAX® 7233 SA 01 MED, PEBAX® 7033 SA 01 MED, PEBAX® 6333 SA 01 MED, PEBAX® 5533 SA 01 MED, PEBAX® 4533 SA 01 MED, PEBAX® 4033 SA 01 MED, PEBAX® 3533 SA 01 MED, PEBAX® 2533 SA 01 MED, and PEBAX® MV 1074 SA 01 MED manufactured by Arkema, Inc, or VESTAMID® Care ME71, VESTAMID® Care ME62, VESTAMID® Care ME55, VESTAMID® Care ME47, VESTAMID® Care ME40, and VESTAMID® Care ME26 manufactured by Evonik Corporation. However, it is to be understood that the heat shrink tubings provided herein are not limited to PEBA resins and may be prepared using one or more of the polymeric resins described herein in addition to PEBA, or instead of PEBA. As described herein, particular embodiments of the disclosed heat shrink tubings may comprise, consist essentially of, or consist of PEBA; and such heat shrink tubings may be referred to herein as "non-crosslinked PEBA heat shrink tubings" or simply "PEBA heat shrink tubings."

In some embodiments, one or more additives can be incorporated within the bulk of the tubing walls, and/or applied upon the inner diameter and/or outer diameter surface. In some such embodiments, the one or more additives can be distributed (e.g., substantially uniformly) throughout the wall thickness and length of the tubing. In some embodiments, the one or more additives may include a lubricant, e.g., such as a thermally stable extrusion process lubricant. In certain embodiments, the lubricant may be a pentaerythritol ester, such as GLYCOLUBE® from Azelis Americas, LLC, for example. In some embodiments, the one or more additives may include a radiopaque filler (i.e., an inorganic radiocontrast agent) to assist in medical procedures that utilize fluoroscopy for navigation of a medical device within the body. In certain embodiments, the radiopaque filler may be barium sulfate ($BaSO_4$), bismuth subcarbonate ($Bi_2O_2CO_3$), bismuth oxychloride (BiOCl), bismuth trioxide ($Bi_2O_3$), or tungsten (W), for example. In some embodiments, the one or more additives may include a pigment to provide a desired color of the final PEBA heat shrink tube. In some embodiments, other additives such as inert fillers, stabilizers (i.e., radiation stabilizers, antioxidants, etc.), conductive fillers, anti-tack agents and antimicrobials may be included to produce desired functionality of the final PEBA heat shrink tube for specific applications. The amount of additive that can be contained in the final PEBA heat shrink tube is not particularly limited. In some embodiments, for example, the one or more additives (e.g., lubricant, pigment, filler, etc.) may be included in an amount in the range of about 0.1% to about 80%, about 1% to about 30%, or about 5% to about 20% by weight based on the total weight of the PEBA heat shrink tube. In other embodiments, the PEBA heat shrink tubes may not include any additives therein.

The sizes of heat shrink tubes within the scope of this disclosure (e.g., length, diameter (i.e., expanded inner diameter, ID), and average wall thickness) are not particularly limited. For example, the length of tubes described herein can vary from individually-sized units (e.g., in some embodiments, on the order of 0.1 inches to 120 inches for catheter or medical device component manufacturing) to lengths that can readily be transported and further cut into individually-sized units to large-scale production lengths (e.g., on the order of hundreds of feet and the like). The diameters of tubes described herein can vary, in particular, depending upon the application for which the tubing is intended. Certain expanded IDs of the tubes described herein, particularly for catheter and medical device uses, can range from about 0.005 inches to about 1.5 inches (e.g., about 0.01 inches to about 0.7 inches or about 0.015 inches to about 0.5 inches), although tubes having expanded IDs outside this range are also encompassed by the present disclosure, particularly in the context of applications in different fields.

In general, the methods by which heat shrink tubes are prepared can vary. Generally, the desired resin or resins, such as the PEBA resins as described herein, are converted into a tubular form via extrusion and then mechanically expanded. The means by which these steps are conducted can vary, as will be described herein.

A resin (e.g., such as a PEBA resin) may be formed into a tube by subjecting the resin to extrusion. Extrusion generally comprises placing the desired resin or resins into an extruder (e.g., a single screw melt extruder). Within the extruder, the resin or resins are heated, compressed, and forced through an annular die set, creating a tube. The annular die set (also referred to herein as "tooling") consists of a circular extrusion die and a mandrel which forms the polymer melt into a tubular form as it exits the extruder. Tubes of various diameters, wall thicknesses, and lengths can be produced using the forming methods described herein. The final dimensions of the extruded tubular form can be adjusted and optimized through proper tooling selection along with other parameters in the extrusion step such as temperature, pressure, and screw rotation speed. The tube-forming tooling is fitted to the extrusion head (i.e., the end) of the extruder which is generally comprised of a hopper, barrel, screw, breaker plate, and extrusion head. The screw of the extruder is generally comprised of several sections (e.g., the feed, compression, and metering zones) that can be optimized to provide an effective and consistent extrusion process. Generally, there are multiple temperature-controlled zones throughout the extruder, each of which can be adjusted and optimized to produce tubular forms of desired dimension and quality. In some embodiments, tubing having a relatively uniform wall thickness (i.e., high percent concentricity) is provided.

Appropriate sizing of the annular die set to be used during the extrusion process is generally determined by the specified finished tubular dimensions, extruder specifications, the desired draw down ratio (DDR), and the draw ratio balance (DRB). The DDR and DRB are unitless quantities used by those skilled in the art to describe the relationship between the dimensions of the polymer melt as it exits the annular die set to the dimensions of the final tubular form (i.e., the final extruded tube dimensions). Draw down ratio (DDR) is defined as the ratio of the cross-sectional area of the polymer melt as it exits the annular die set to the cross-sectional area of the final tubular form. The molten tubular form must be "drawn down" (i.e., reduced in diameter and cross-sectional area via stretching) after exiting the annular die set and before quenching (i.e., rapidly cooling in air or a chilled fluid bath) to obtain the desired final tubular dimensions. Generally, utilizing an annular die set that provides a high DDR with respect to the dimensions of the final tubular form enables faster line speeds (i.e., a faster production rate). It is also important to note that a tube produced with a higher DDR has a greater degree of longitudinal orientation of the polymer chains than a tube produced using a lower DDR. It is well known to those skilled in the art that imparting a particular degree of orientation on a polymeric material can influence the mechanical and physical properties of the final product. These properties (e.g., such as mechanical properties) can be optimized for a particular application (i.e., input for a secondary expansion process) by varying the degree of orientation. Draw ratio balance (DRB) is defined as the diameter ratio of the extrusion die and mandrel divided by the diameter ratio of the final tubular form. Generally, DRB characterizes the relationship between the annular shape of the polymer melt as it exits the die and the annular shape of the final tubular form. It is well known by those skilled in the art that careful tooling selection is required to achieve a stable tubular extrusion process. The dimensional relationship of the tooling used to produce a tube of a given size influences the line speed of the extrusion process (i.e., the production rate) based on the DDR. However, this dimensional relationship must be balanced because it also directly influences the overall stability of the extrusion process through the DRB. Tooling selection is an important aspect of the extrusion process to produce a tubular form of specified dimension that also has desirable mechanical characteristics.

The extruded tubular form is then typically radially expanded (e.g., by mechanical means) to provide an expanded tube, i.e., a heat shrink tube (i.e., a tubing which decreases in diameter when heated). The expansion of the input tubing (i.e., the initial extruded tubular form) can be conducted in-line with extrusion or off-line (i.e., conducted independently of and/or secondary to the extrusion process). All means for radial expansion of tubing are intended to be encompassed by the present invention. Generally, during the expansion process, the tubing is expanded radially by pressurizing the inside of the tubing, introducing stress into the tube wall. This pressurizing can be conducted by any means capable of providing a differential pressure between the inside and outside of the tubing. Such differential pressure can be created by imposing a pressure above atmospheric pressure on the inside of the tube, imposing a pressure below atmospheric pressure on the outside of the tube, or a combination of the two. The stress induced into the wall of the tube causes it to expand radially, i.e., increase in diameter. The rate of expansion can be controlled so the tube will hold the expanded state and does not recover until subjected to a further heat cycle. The extent to which a tube is expanded depends on the application for which the final heat shrink tubing is intended. The rate and extent to which a tube is expanded depends on the temperature at which the expansion process is conducted. It has been found that the expansion chamber temperature must be carefully controlled to optimize the rate and extent of expansion of the tube. In some embodiments, the tubing is expanded to an inner diameter from about 1.05 times its original (unexpanded) inner diameter to about 10 times its original (unexpanded) inner diameter.

In certain embodiments, PEBA heat shrink tubes prepared according to the present disclosure may be radially expanded using the processes described, for example, in U.S. Pat. No. 9,296,165 to Henson, which is incorporated by reference herein in its entirety. For example, the Henson patent describes a process for the production of thermoplastic polymeric heat shrink tubing using a first fluid in the interior of a tube to expand it and a second fluid exterior to the tube to constrain the expansion within an expansion chamber. In other embodiments, for example, the tubing may be expanded by adjusting the flow rate of the air external to the tube, the chamber temperature, the air pressure within the tube, and the rate at which the tube moves through the expansion chamber. In certain embodiments, the heat shrink tubes of the present disclosure are expanded at elevated temperature through a die using any number of methods known to the art, and subsequently cooled at the die exit. Cooling can be accomplished using fluids such as water, oil, or air. The processing parameters that can be adjusted include, but are not limited to: die type, die diameter and length, die temperature, fluid pressure inside the tube, fluid pressure outside the tube, cooling method, cooling medium type and temperature, expansion rate, tube material, tube ID, tube OD, and tube wall thickness.

It is noted that, although certain heat shrink PEBA tubes are known, these tubes comprise predominantly crosslinked PEBA, which provides for the heat shrink capabilities of the tubes. Generally, the PEBA heat shrink tubes provided herein are expanded under carefully controlled conditions of internal air pressure, temperature, and throughput through an expansion die prior to rapidly cooling the tube to lock in the entropically unfavorable expanded state. Examples of heat shrinkable crosslinked PEBA tubing are provided, for example, by Cobalt Polymers, TE Connectivity, and in the disclosures of U.S. Pat. No. 7,306,585 to Ross and U.S. Pat. App. Pub. No. 2008/0317991 to Pieslak et al. Crosslinking through chemical means or by irradiation has long been used in the production of heat shrink tubes and films in order to obtain a greater degree of elastic recovery of the expanded part upon heating (i.e., increase attainable recovery ratio and/or recovery force upon heating). Crosslinking a polymer article such as a tube or film effectively increases the molecular weight of the polymer in addition to improving its elastic response to an imposed deformation. This effective increase in molecular weight also results in a marked increase in the viscosity of the polymer (due to the increased probability of interchain entanglements), which hinders the ability of the material to flow into and fill voids (i.e., open spaces or interstices in the pattern of an underlying reinforcing component). The increased viscosity due to crosslinking also reduces the ability of the polymer to conform tightly to and bond with an underlying substrate during recovery. The increased recovery ratio attainable with crosslinked materials can also lead to unwanted deformation or damage to a sensitive underlying substrate during recovery (i.e., delicate laser-cut hypotubes).

Advantageously, as referenced herein, heat shrink tubes comprising PEBA are provided, wherein a majority (e.g., the entirety) of the PEBA within the tube is not cross-linked. In some embodiments, the tubes provided herein comprise no cross-linked polymer, comprise less than about 2% by weight of a crosslinked polymer, less than about 1% by weight of a cross-linked polymer, or less than about 0.5% by weight of a cross-linked polymer. The disclosed heat shrink tubes can exhibit high recovery ratios; in some embodiments, the disclosed heat shrink tubes can have recovery ratios (RRs) of greater than about 1.05:1, greater than about 1.10:1, greater than about 1.2:1, greater than about 1.3:1, greater than about 1.4:1, greater than about 1.5:1, or greater than about 1.6:1, e.g., about 1.05:1 to about 2:1. In some embodiments, the heat shrink tubes can be described based on the reducibility in ID (upon recovery). Examples of such values include, but are not limited to, tubes reducible in ID by at least about 4%, at least about 5%, at least about 6%, at least about 7%, at least about 8%, at least about 9%, at least about 10%, at least about 11%, at least about 12%, at least about 13%, at least about 14%, at least about 15%, at least about 20%, at least about 25%, or at least about 30%, such as about 5% to about 40%, including, e.g., about 4.8%, about 9.1%, about 16.7%, about 23.1%, about 28.6%, about 33.3%, or about 37.5%.

In some embodiments, the disclosed heat shrink tubes can be described based upon their durometer hardness measurements. For example, in one specific embodiment, a durometer hardness measurement of a heat shrink tubing as provided herein according to ASTM D2240 conducted on a flat specimen fabricated by melt pressing the heat shrink tubing (in expanded form) is about 20 to about 80 shore D.

The heat shrink tubes provided herein can be used in various ways. In some embodiments, they are advantageously used in catheter assembly processes, e.g., as a replacement for conventional (e.g., FEP) heat shrink tubings used as manufacturing aids to compress an underlying catheter pre-assembly during heating/reflow. Such processes can avoid the need for disposable components, e.g., the FEP heat shrink tubings typically required to produce the catheter assembly. According to the present disclosure, the provided heat shrink tubes (e.g., PEBA heat shrink tubes) can function both as a catheter jacket and as a processing aid/heat shrink to provide sufficient compression during heating/reflow.

As such, the disclosed heat shrink (i.e., expanded) tube enables a catheter shaft to be manufactured by heating the heat shrink tube as an outer layer ("jacket") of a catheter shaft pre-assembly, inducing dimensional recovery of the heat shrink tube and allowing for reflow through a reinforcing component (where present) and bonding to the underlying liner without the use of a fusing sleeve (e.g., FEP). Since the polymeric material of the disclosed heat shrink tube is not crosslinked, its viscosity is such that the polymer can easily flow through and encapsulate a reinforcing component (where present) and adhere to the outer surface of the inner liner when heated under an appropriate recovery profile. The selection of an appropriate heating temperature and time (also referred to herein as "heating profile" or "recovery profile") for a particular non-crosslinked heat shrink outer jacket tube can vary substantially depending on the underlying catheter assembly components and the composition of the non-crosslinked heat shrink tubing. In particular applications, the recovery ratio can also be tailored along with the recovery profile to provide a catheter shaft where the outer jacket only bonds to the outer surface of a reinforcing component, leaving the underlying interstices open to allow for a catheter shaft with increased flexibility. In this way, expansion conditions, recovery ratio, and the recovery profile can be tailored to provide a non-crosslinked PEBA heat shrink tube capable of forming an outer sheath for various different types of catheter structures.

The present disclosure also enables a catheter shaft to be manufactured by heating the non-crosslinked heat shrink tube over a laser-cut hypotube that induces dimensional recovery of the tube such that it bonds with the outer surface of the laser-cut hypotube without flowing within the interstices of the laser-cut structure. The recovery ratio and recovery profile can be tailored to provide a sufficiently bonded outer jacket for these types of catheter shafts. The recovery process can also be optimized to preserve the mechanical characteristics engineered into the design of a laser-cut hypotube reinforcing structure. The traditional catheter manufacturing process 10 utilizing an FEP fusing sleeve to reflow an outer jacket tube provides a relatively high recovery force. This high recovery force, coupled with the high recovery temperature of FEP heat shrink, forces the molten outer jacket tubing to flow through the interstices of underlying reinforcing components. Typically, for applications comprising braided or coiled reinforcing structures, this would be a desirable outcome of the reflow process 10. However, in certain embodiments involving laser-cut hypotubes, it is not desirable for the heat shrink material to flow within the laser-cut interstices during the heating step 16. To achieve varying degrees of flexibility along the length of a catheter shaft, medical device engineers can adjust or alter the pattern that is laser-cut through the walls of the hypotube. For this particular application, if the outer jacket flows within the interstices during heating step 16, the outer jacket material that infiltrates the interstices prevents the laser-cuts from deforming as designed; permanently reducing the flexibility of the finished shaft. In this particular embodiment, it is desirable for the outer jacket to bond with the outer surface of the laser-cut hypotube without infiltrating and disrupting the flexibility of the laser-cut structure. This is realizable due to the ability of PEBA materials to bond to metallic substrates.

In one embodiment, the disclosed heat shrink tube can be utilized in a semi-automated process to manufacture a covered laser-cut hypotube catheter shaft. For example, after the laser cutting of the hypotube is completed, it can be directly fed from the cutting operation into a discrete length of the disclosed heat shrink tube. After insertion, the laser-cut hypotube and heat shrink tube can be exposed to a heat source to dimensionally recover the heat shrink tube and bond to the outer surface of the laser-cut hypotube (i.e., forming a covered laser-cut hypotube). This heating step can be done either in-line in a continuous process, or in a semi-automated process where the laser-cut hypotube is fed into the disclosed heat shrink tube and manually transferred to a heat source to complete the build. It is also envisaged that long lengths of hypotube can be laser-cut and continuously inserted into a long length, coil, or spool of disclosed heat shrink tubing. This pre-assembly can be subsequently fed into an oven or other heat source to recover and bond the heat shrink tubing to the outer surface of the laser-cut hypotube. After heat exposure, the covered laser-cut hypotube can be cut into discrete lengths to finalize the build. Alternatively, the pre-assembly can be cut into discrete lengths before being exposed to a heat source to recover and bond the disclosed heat shrink tubing to the outer surface of the laser-cut hypotube.

After production of the desired construct with the disclosed heat shrink tube associated therewith and during or after recovery of the heat shrink tube, if desired, the outer surface of the construct (comprising the heat shrink material) can optionally be further modified or smoothed through a secondary process. For example, in some embodiments, the construct is passed through a heated metallic die or a heated polymer-coated die during or after recovery of the heat shrink material, producing a catheter assembly comprising a modified (e.g., smoothed) outer surface. The heated die can be coated with polytetrafluoroethylene (PTFE), for example. In some embodiments, the construct is passed through a heated or polymer-coated die during or after recovery of the heat shrink material to provide a textured or engineered outer surface to modify or enhance sliding properties of the finished construct.

Figure 1B:
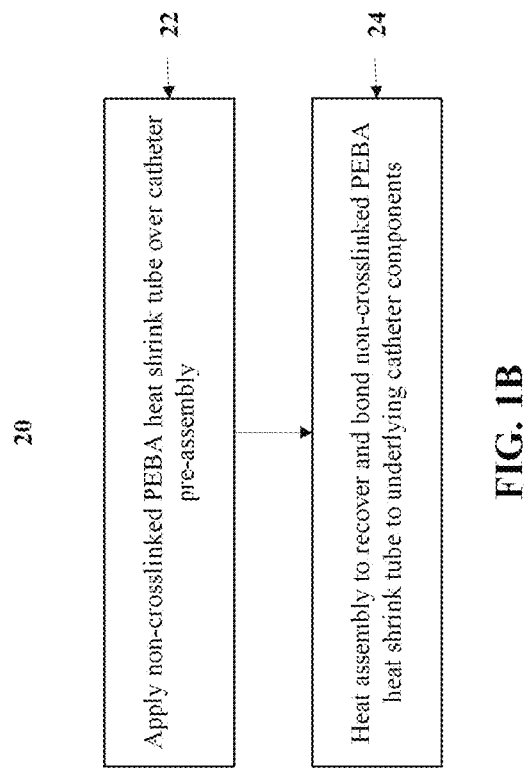
Figure 2:
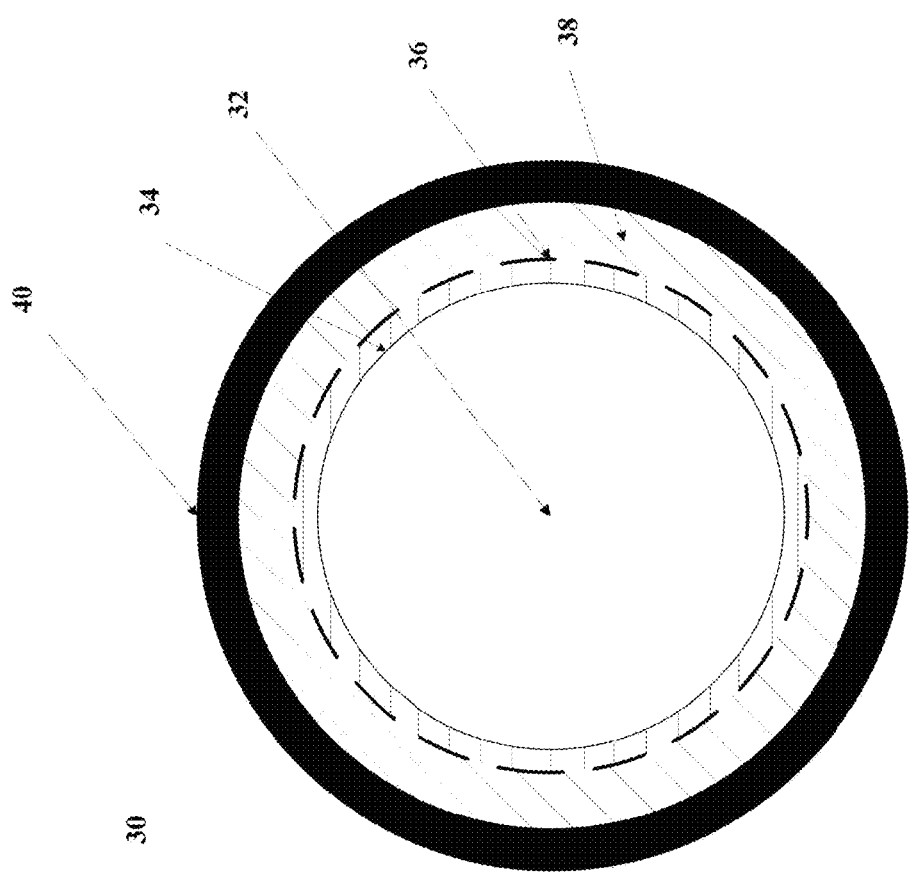
FIG. 2 is a cross-sectional diagram of a typical reinforced single lumen catheter assembly after the heating step 16 of the reflow process 10 and before removal of the FEP heat shrink fusing sleeve 40. The layers of the composite structure are the solid core/mandrel/inner lumen 32, the thin-walled liner 34, the reinforcing component 36, the outer jacket 38, and the FEP heat shrink manufacturing aid 40.
Figure 3:
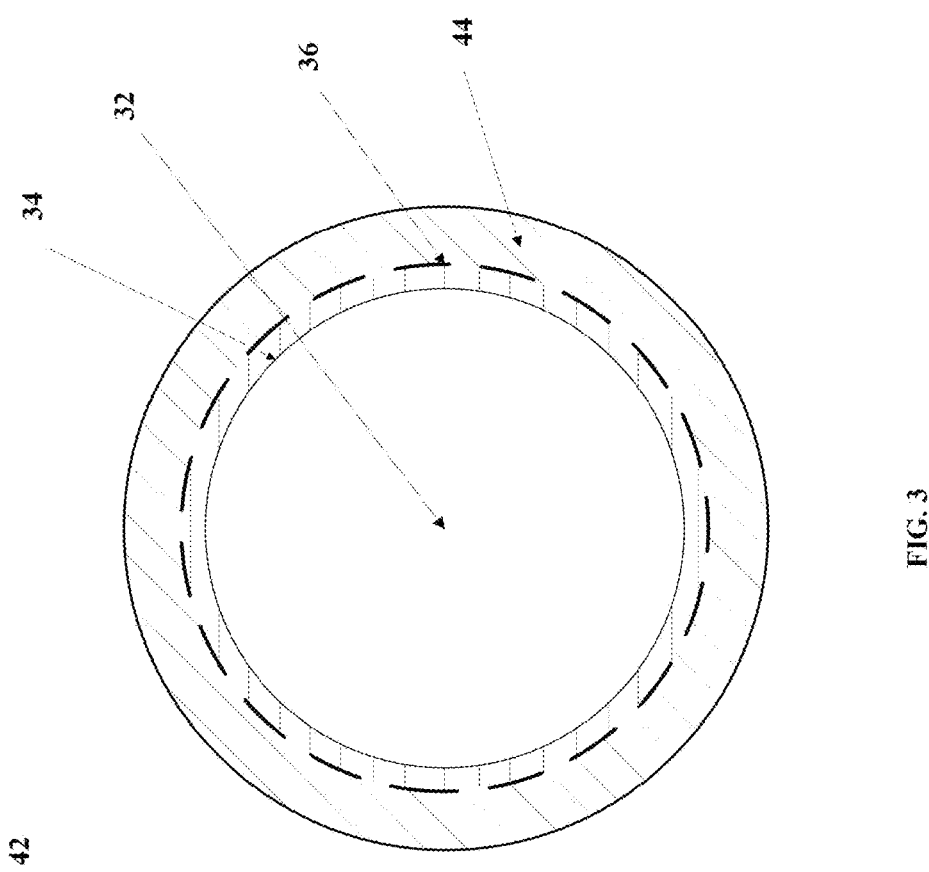
FIG. 3 is a cross-sectional diagram of an example of a reinforced single lumen catheter assembly after the heating step 24 of the recovery process 20 that bonds the non-crosslinked PEBA heat shrink to the outer surface of the underlying components. The layers of the composite structure are the solid core/mandrel/inner lumen 32, the thin-walled liner 34, the reinforcing component 36, and the non-crosslinked PEBA heat shrink outer jacket 44.

The present disclosure enables the replacement of a traditional dual-layer outer jacket assembly 30 comprising a FEP fusing sleeve 40 and non-heat shrinkable PEBA outer jacket tube 38 that is used in conventional reflow methods 10. See FIGS. 1A and 2. These traditional components and processing techniques can be replaced with a single-layer outer jacket assembly 42 comprising a single non-crosslinked PEBA heat shrink tube as provided herein, which functions as a heat shrink outer jacket tube 44. See FIG. 3. The non-crosslinked PEBA heat shrink tube can be used in a recovery process 20 (see FIG. 1B). The use of the disclosed heat shrink tubing as an outer jacket for catheter shafts eliminates the need for manufacturing aids such as FEP heat shrink tubes commonly used in the production of catheter shafts. This is advantageous in many respects. Firstly, an expensive component is removed from the manufacturing process. Secondly, process scrap is reduced since the FEP heat shrink tubing must be removed and discarded after the reflow process is completed. Thirdly, the heat transfer of the recovery process is improved greatly by removing, in effect, an insulating layer (i.e., the FEP heat shrink tubing), which will improve cycle times. Finally, the potential for damaging the completed catheter shaft during manufacturing is greatly reduced if there is no need to nick, skive, or cut away an FEP heat shrink tube in order to remove it.

Furthermore, this replacement will greatly improve the efficiency and cost effectiveness of a catheter shaft manufacturing process by shortening heating cycle times, labor costs by removing process steps, and reducing component costs. The efficiency improvement that the presently disclosed PEBA-based heat shrink tube enables in terms of heating cycle time can be envisioned by comparing the heat transfer rate achieved during the heating step 16 of a conventional reflow process 20 comprising a dual-layer outer jacket assembly 30 (see FIG. 1A and FIG. 2), to the heat transfer rate during the heating step 24 of a recovery process 20 comprising a single-layer outer jacket assembly 42 (see FIG. 1B and FIG. 3). The heat transfer rate is a quantity that provides the amount of heat that is transferred through a material per unit time, under given circumstances. In the example calculations provided herein below, the tubular outer jacket assembly has a heat source that is positioned external to the outer surface of the assembly such that heat flows radially inward from the source, through the wall layer(s) of the assembly, and towards the inner surface of the assembly. This analysis was performed through an idealized application of Fourier's Law of Conduction using a cylindrical coordinate system. See e.g, DOE Fundamentals Handbook: Thermodynamics, Heat Transfer, and Fluid Flow," DOE-HDBK-1012/2-92, U.S. Department of Energy, June 1992, which is incorporated herein by reference. Several assumptions are made in order to apply the following equations, including: the heat source is in intimate contact with the entirety of the circumference of the outermost surface for both considered cases, all surfaces are in intimate contact with adjacent surfaces, the thermal conductivity for each layer is assumed to be constant as a function of temperature, and heat losses to the surrounding environment and catheter components underlying the outer jacket assembly is considered to be negligible. With the above assumptions considered, the heat transfer rate can be calculated using Equation 1, a form of Fourier's Law of Conduction, that allows for the determination of the heat transfer rate through a tubular wall of known thermal conductivity and dimension:

$$\dot{Q} = kA_{lm}\left(\frac{\Delta T}{\Delta r}\right) = \frac{2\pi k L(\Delta T)}{\ln(r_o/r_i)} \quad (1)$$

Where: k is the thermal conductivity of the tubular wall
$A_{lm}$ is the log-mean cross-sectional area of heat transfer
$\Delta T$ is the temperature difference between the inside and outside of the tube
$\Delta r$ is the difference in radius between the outer surface ($r_o$) and the inner surface ($r_i$) of the tube wall
L is the longitudinal length of the heat source Equation 1 can be expanded to allow for the determination of the heat transfer rate through the composite wall of a dual-layer tube, as shown in Equation 2:

$$\dot{Q} = \frac{2\pi L(\Delta T)}{\frac{\ln(r_2/r_1)}{k_1} + \frac{\ln(r_3/r_2)}{k_2}} \quad (2)$$

Where: $k_1$ and $k_2$=the thermal conductivity of the inner and outer layers, respectively
$r_1$=radius of the innermost surface (ID of the inner layer tube)
$r_2$=radius of the interface surface (OD of inner layer, ID of outer layer)
$r_3$=radius of the outermost surface (OD of the outer layer tube)

Equation 1, along with the aforementioned assumptions and parameters to be described more fully, can be used to determine the heat transfer rate through a single non-crosslinked PEBA heat shrink layer 44 during the heating step 24 of a recovery process 20. The dimensional parameters and heat transfer rate for this single-layer outer jacket assembly is designated as Case 1 in Table 1. Equation 2 can be used similarly to determine the heat transfer rate through a dual-layer outer jacket assembly 30 comprising a FEP fusing sleeve 40 and a non-heat shrinkable PEBA outer jacket tube 38 during the heating step 16 of a conventional reflow method 10. The heat transfer rate for this dual-layer outer jacket assembly is designated as Case 2 in Table 1. These cases were considered to compare the difference in the heat transfer rate between the heating step 16 of a conventional "reflow" catheter manufacturing process 10 and the heating step 24 of a "recovery" method 20 that the present invention enables. This analysis assumed a heat source length (i.e., longitudinal region of heat transfer) of 10-mm. The temperature difference between the heat source and inside of the tubular structure was assumed to be 187K (i.e., the temperature difference when the heat source temperature is at a typical FEP HS recovery temperature of 210° C. (483.15 K) and the inside of the catheter assembly is assumed to be approximately room temperature, 23° C. (276.15 K)). The thermal conductivity of PEBA was assumed to be 0.180 W/m·K and the thermal conductivity of FEP was assumed to be 0.180 W/m·K. See, e.g., https://www.matweb.com/search/datasheet.aspx?matguid=5a22f9b853e64148b0ffab9d3d1da a5a&n=1&ckck=1, D. M. Price, M. Jarratt, *Thermochimica Acta*, 392, 231, 2002 and L. K. Olifirov, A. A. Stepashkin, G. Sherif, V. V. Tcherdyntsev, *Polymers*, 13, 781, 2021, which are incorporated herein by reference in their entireties. The dimensional attributes used for the determination of the heat transfer rate for both cases considered are shown in Table 1. Under the considered parameters, the heating step 24 of a recovery process 20 enabled by the non-crosslinked PEBA heat shrink tubes of the present invention increases the heat transfer rate by around 82% compared to the heating step 16 of a traditional "reflow" manufacturing process 10. This is an advantageous aspect of the currently disclosed tubes and methods for catheter shaft manufacturers not only for throughput efficiency, but also for collective energy and resource conservation. Furthermore, process efficiency will be increased through the reduction of labor costs by removing step 14 and step 18 of the traditional reflow process 10. In addition to process efficiency, removing the need for a disposable and costly FEP heat shrink manufacturing aid is supportive of reducing the environmental impact of these manufacturing processes through reduction of scrap.

TABLE 1

Heat Transfer Rate

| Case | PEBA ID [mm] | PEBA OD [mm] | FEP OD [mm] | Heat Transfer Rate [W] |
|---|---|---|---|---|
| 1 | 2.00 | 2.50 | — | 9.48 |
| 2 | 2.00 | 2.50 | 3.00 | 5.22 |

Heat shrink tubes provided herein can be used for a range of applications. In particular applications, heat shrink tubes as provided herein can be applied to an underlying material (e.g., devices, device components, joints, fittings, wires, etc.), and heated (i.e., recovered) to form a covering thereon. Accordingly, the present disclosure encompasses materials or objects to which a tube as disclosed herein has been applied. For example, in some embodiments, a covered device (e.g., medical device) comprising a heat shrink tube (e.g., in recovered form) as disclosed herein is provided. Exemplary covered devices include, but are not limited to, medical devices (e.g., catheters, catheter shafts, and catheter shaft components) comprising any of the tubes disclosed herein applied thereto (in expanded/non-recovered and recovered forms). In some embodiments, a covered hypotube (e.g., a laser-cut hypotube) is provided.

Constructs employing the disclosed heat shrink tubes can exhibit suitable properties for a range of applications. In some embodiments, constructs comprising the heat shrink tubing provided herein as an outer covering can exhibit good bonding between the heat shrink material and underlying component(s) of the construct. For example, the heat shrink material may provide for good bonding through a reinforcing component (e.g., braid or wire/coil structure) to an underlying liner (which can optionally be surface-modified) in the context of a catheter assembly. The heat shrink material may provide for good bonding to an unreinforced surface-modified PTFE-liner. A surface-modified liner (e.g., a surface-modified PTFE liner) can include, for example, an etched outer surface (e.g., wherein at least a portion of the surface has been sodium etched) and/or can include a liner with a tie layer associated therewith (e.g., a PTFE liner with tie layer thereon). In some embodiments, the construct exhibits a cohesive failure mode when peeled.

Constructs can comprise further components than those explicitly disclosed herein. For example, in some embodiments, the constructs provided herein can further comprise an outer thin-walled tube comprising a heat-shrinkable material different from the disclosed heat shrink tubes, which is placed over the heat shrink tube provided herein. The two tubes can be recovered together over the underlying catheter components to form the outer jacket of the catheter shaft. In this manner, for example, a thin-walled PET heat shrink tube can be used as the outer layer to give a lubricious and glossy surface to the catheter shaft. In some embodiments, an outer thin-walled tube comprising a heat shrinkable material different from the disclosed heat shrink tubes and having poor adhesion to the material of the disclosed heat shrink tubes can be placed over the disclosed heat shrink tube, and the two tubes can be recovered together. In some embodiments, for example, the disclosed heat shrink tube can be inserted into an FEP heat shrink tube and expanded by applying temperature and/or pressure to form a dual layer heat shrinkable tube. In other embodiments, for example, the disclosed heat shrink tube can be inserted into an FEP heat shrink tube and heated to partially recover the outer FEP heat shrink to contact the outer surface of the inner disclosed heat shrink tube while applying pressure to prevent the inner layer from appreciably recovering. After recovery, the outer tube can be removed to give a glossy coated catheter shaft (the glossy coating comprising the material of the disclosed heat shrink tube). Other examples of dual heat shrink structures are provided, for example, in the disclosure of U.S. Pub. Pat. App. No. 2021/0370581 to Hunter et al., which is incorporated herein by reference in its entirety.

Further, one or more surfaces of the disclosed constructs can, in some embodiments, be modified. For example, in some embodiments, the heat shrink material can exhibit enhanced lubricity on an outer surface thereof relative to the as-provided construct (e.g., due to chemical treatment or a further coating applied thereto, e.g., such as a liquid or polymeric coating to enhance the lubricity of the surface). As such, in some embodiments, a construct comprising the disclosed heat shrink material (in recovered form) is provided, which exhibits a hydrophobic surface coating. In some embodiments, the disclosed constructs can comprise one or more additional components, e.g., one or more tie layers between adjacent layers.

In particular embodiments, a catheter pre-assembly is provided which comprises the heat shrink tube of the present disclosure, wherein the heat shrink tube is the outer sheath (other components are included as described elsewhere herein). The disclosure encompasses both the pre-assembly and the final catheter assembly (which is provided after heating and shrinking of the heat shrink tube). A wide range of such catheter assemblies can be provided according to the principles provided herein, including, but not limited to, guide catheters, microcatheters, balloon catheters, and steerable delivery catheters.

In some embodiments, a plurality of heat shrink tubes as provided herein having different durometer hardness (i.e., flexibility) can be joined together (e.g., using tape or adhesive, heat or solvent welding, interference fit, etc.) and placed over a catheter assembly prior to recovery to form a catheter shaft with varying degrees of flexibility and smooth transitions. For example, the plurality of heat shrink tubes can comprise, e.g., two or more, three or more, four or more, five or more, six or more, seven or more, eight or more, nine or more, or ten or more heat shrink tubes with different durometer hardness values. In some embodiments, heat shrink tubes as provided herein having different durometer hardness (i.e., flexibility) can be sequentially placed and recovered over a catheter assembly. The transitions between adjacent heat shrink tubes can be, in some embodiments, smoothed by passing the construct through a heated metallic or polymer-coated die either during or after the forming (i.e., recovery) process is completed to form a catheter shaft with varying degrees of flexibility and smooth transitions. In certain embodiments, heat shrink tubes as provided herein having different durometer hardness (i.e., flexibility) can be sequentially placed and recovered over a catheter assembly; the tubes can optionally be further treated to smooth the transitions between outer jacket sections using an FEP fusing sleeve to form a catheter shaft with varying degrees of flexibility and smooth transitions.

EXPERIMENTAL

Aspects of the present invention are more fully illustrated by the following examples, which are set forth to illustrate certain aspects of the present invention and are not to be construed as limiting thereof. Although the examples shown pertain to non-crosslinked PEBA heat shrink tubing specifically, it is understood that heat shrink tubing comprised of other biocompatible or medical grade polymeric materials would benefit according to the present invention.

Bond Test

Figure 4:
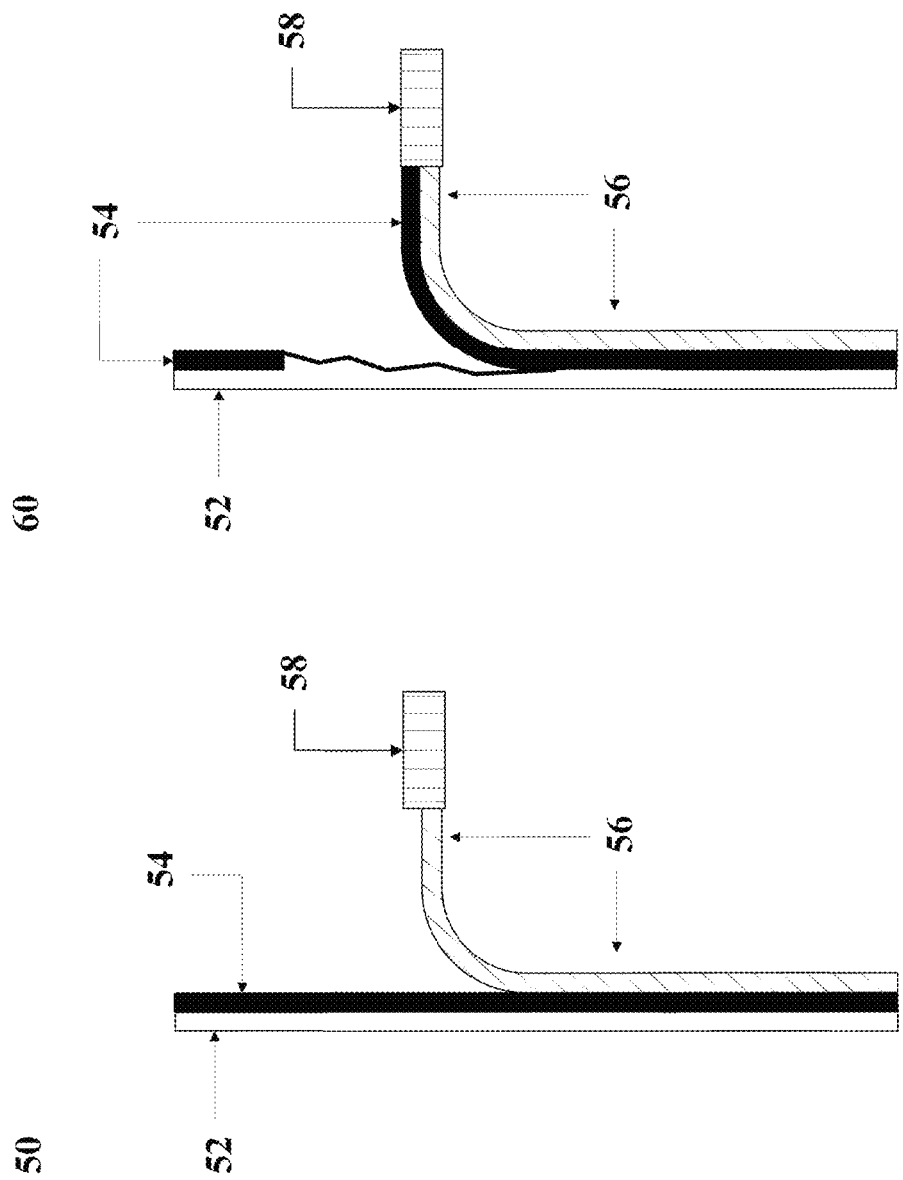
FIG. 4 is an illustrative definition for the adhesive 50 and cohesive 60 failure modes observed for the bond test conducted on prepared sections of unreinforced catheter shafts as described herein according to certain embodiments of the present disclosure. A PEBA outer jacket tube 56 was bonded to the modified outer surface 54 of a PTFE liner tube 52 using the typical reflow catheter shaft manufacturing method 10 for a non-heat shrinkable outer jacket or the recovery catheter shaft manufacturing method 20 for a heat shrinkable outer jacket. Before bonding, an aluminum foil tab 58 was placed between the PEBA tube 56 and the modified outer surface 54 of the PTFE liner tube 52 to prevent bonding at the end of the sample to provide a tab from which to peel the layers apart. A single longitudinal slit was cut with a razor blade through one wall of the prepared lengths of unreinforced catheter shafts and flattened to give a generally rectangular peel specimen. The specimens were then peeled by hand and visually inspected to determine if an adhesive failure mode 50 or cohesive failure mode 60 occurred while peeling away the interface between the modified outer surface 54 of the PTFE liner tube 52 and the PEBA tube 56.

A method relying on the physical examination of a test specimen after conducting a 'bond test' was used to determine if an adequate bond was created between the outer surface of an inner liner tube and the inner surface of an outer jacket tube. Various elements of this method are illustrated in FIG. 4, and numerals correspond to such various elements as described more fully below. This method involves fabricating a short section of an unreinforced catheter shaft, e.g., approximately 4 to 6 inches in length. Several examples were fabricated using heat-shrinkable and non-heat-shrinkable PEBA tubing as the outer jacket 56. This allows for a comparison of the bond that is formed between the outer surface 54 of the PTFE liner tube 52 and the inner surface of the PEBA outer jacket tube 56 when a FEP fusing sleeve is utilized versus the non-crosslinked PEBA heat shrink tubing of the present invention. Preparation of the bond test specimens began by fabricating an unreinforced catheter shaft subassembly for each Example that was tested. Fabrication began by hand stretching a PTFE liner tube 52 with a modified (i.e., sodium etched) outer surface 54 having an inner diameter of about 0.078" and an average wall thickness of about 0.0015" over a stainless-steel mandrel having an outer diameter of about 0.075". This stretching step forces the PTFE liner tube 52 to "draw down" and fit snugly over the metallic mandrel, resulting in an unreinforced catheter shaft subassembly. A 1-inch-long thin strip of aluminum foil 58 was wrapped around one end of the subassembly (i.e., on the outside surface 54 of the PTFE liner tube 52) to prevent bonding between the outer surface 54 of the PTFE liner tube 52 and the inner surface of the PEBA outer jacket tube 56 where the foil 58 was applied. The inclusion of the 1-inch-long aluminum foil strip 58 serves to provide a "tab" from which to peel apart the inner PTFE liner tube 52 and PEBA outer jacket tube 56 after the build was completed. For bond test specimens fabricated using a heat shrinkable PEBA tube as the outer jacket 56, the PEBA heat shrink outer jacket tube 56 was applied over the subassembly and aluminum foil strip 58, suspended vertically from an oven rack using clips, and heated in a standard laboratory gravity convection oven to finalize the build. For bond test specimens fabricated using a non-heat-shrinkable PEBA tube as the outer jacket 56, an FEP heat shrink tube having an expanded inner diameter of about 0.119", a wall thickness of about 0.008", and a recovered inner diameter of 0.072" was applied over the PEBA outer jacket tube 56, suspended vertically from an oven rack using clips, and heated in a standard laboratory gravity convection oven to finalize the build. After heating the specimens for the time and temperature noted in Table 3, they were allowed to cool to room temperature and subsequently removed from the metallic mandrel. The FEP heat shrink tube was skived from the build for the bond test specimens prepared using a non-heat shrinkable PEBA outer jacket. After removal, the unreinforced catheter shaft specimen was slit longitudinally on one side using a razor blade and flattened to give a 'rectangular' shape. It is important to note that the aluminum foil tab 58 typically bonds to the PEBA outer tube 56 after heating but does not bond to the modified outer surface 54 of the PTFE liner tube 52. The bond test was performed by grasping in one hand the tab end of the PTFE liner tube 52 (i.e., the portion that was underneath the aluminum foil 58) and the aluminum foil tab 58 attached to the PEBA tube 56 in the other hand and slowly pulled in opposite directions for approximately 2-inches.

After peeling, careful examination of the section of PTFE liner tube 52 that was peeled away from the PEBA outer jacket tube 56 can aid in determining if an adequate bond was created between the modified outer surface 54 of the PTFE liner tube 52 and the inner surface of the PEBA outer jacket tube 56. There are well known methods to those skilled in the art involving the modification of the outer surface of thin-walled PTFE tubings to allow for bonding with other materials. The surface modification methods employed for the PTFE liner tubes used herein did not involve the application of a tie-resin, though it is understood that combining such technology with the non-crosslinked PEBA heat shrink tubes of the present invention will substantially increase the bond strength between the liner tube and outer jacket. Typically, this surface modification (i.e., etching) changes the color of the outer surface 54 of the PTFE liner tube 52 from a natural transparent-white/blue to a translucent-brownish/amber color. If the PEBA outer jacket tube 56 did not adequately bond to the outer surface 54 of the PTFE liner 52 during the heating step, none of the modified outer surface 54 of the PTFE liner 52 will be transferred to the PEBA outer jacket tube 56 when it is peeled away in the manner described above (i.e., resulting in an "adhesive" peel mode 50, as illustrated in FIG. 4). It can be inferred through this test that an inadequate bond was formed during the heating step if the PTFE liner 52 is easily peeled away from the PEBA outer jacket tube 56 (i.e., there is little or no resistance to peeling the layers apart). Furthermore, it can be inferred that an inadequate bond was formed if there is little to no color difference between the portion of the PTFE liner 52 that was covered by the aluminum foil tab 58 and the portion of the PTFE liner 52 that was peeled away from the PEBA outer jacket tube 56 (i.e., both portions of the PTFE liner 52 remain a translucent-brownish/amber color). However, if the PEBA outer jacket tube 56 did adequately bond to the outer surface 54 of the PTFE liner 52 during the heating step, some of the modified outer surface 54 of the PTFE liner 52 will be transferred to the PEBA outer jacket tube 56 when it is peeled away in the manner described above (i.e., resulting in a "cohesive" peel mode 60, as illustrated in FIG. 4). It can be inferred through this test that an adequate bond was formed during the heating step if it is difficult to peel the PTFE liner 52 away from the PEBA outer jacket tube 56 (i.e., there is some resistance or substantial resistance to peeling the layers apart). Furthermore, it can be inferred that an adequate bond was formed if there is a noticeable color difference between the portion of the PTFE liner 52 that was covered by the aluminum foil tab 58 and the portion of the PTFE liner 52 that was peeled away from the PEBA outer jacket tube 56 (i.e., the "tab" portion of the PTFE liner 52 remains a translucent-brownish/amber color and the portion of the PTFE liner 52 that was peeled away from the PEBA outer jacket tube 56 becomes a transparent/translucent-white/blue color). A summary of the results from the bond tests performed on various Examples are summarized in Table 3.

Durometer Hardness (Shore D)

Durometer Hardness is a useful quantity that is often measured for polymeric materials as it generally relates to the flexibility of the material being tested. For example, a sample that has a lower durometer value indicates that it is comprised of a more flexible, less rigid material than a sample having a higher durometer value. Specimens suitable for a durometer hardness test (i.e., of sufficient thickness) were fabricated by compression molding Example tubes with a manual bench top hydraulic press manufactured by Carver, Inc. The Example tubes were cut into short pieces and thoroughly dried in a standard laboratory gravity convection oven before molding. The dried tubes were placed into a 4"×4"×0.04" stainless steel mold and melt pressed between heated caul plates at approximately 15,000 pounds of clamping force to produce flat plaque specimens of relatively uniform thickness. The pressed samples were cut into 6 equivalent pieces and stacked to provide a durometer hardness test specimen having a thickness of about 0.24". The durometer hardness of the stacked specimen was then measured using a Type D indenter per ASTM D2240-15: *Standard Test Method for Rubber Property—Durometer Hardness*, 2015. The average of 5 measurements for the Examples tested is shown in Table 4.

Comparative Example 1

A commercially available poly(ether-block-amide) (PEBA) resin (Arkema, Inc, PEBAX® 7233 SA 01 MED) was obtained in pellet form and dried in an oven at 167° F. overnight to ensure the resin moisture content was less than about 0.15% by weight. The dried resin was placed into a heated resin hopper under a nitrogen blanket to prevent re-absorption of moisture before extrusion. The dried pellets were extruded into a tubular form by utilizing a single screw extruder having a barrel diameter of 18 mm, a screw rotation of about 10 rpm, a die temperature of approximately 350° F., and an annular die set that provided a draw down ratio (DDR) around 14. After exiting the annular die set, the tube was passed through a chilled water bath to sufficiently quench the tubing and set the final tubular dimensions. The measured dimensional attributes of the produced non-crosslinked PEBA tubes are shown in Table 2. These tubes are not expanded (so will not recover when heated). Comparative Example 1 (and 2) were prepared and evaluated to demonstrate, e.g., that the secondary expansion step of the application example tubes leads to differentiation in the product and that the application example tubes are not crosslinked.

A bond test specimen was prepared using the tubes of Comparative Example 1 along with a FEP heat shrink fusing sleeve. The prepared unreinforced catheter shaft assembly was heated for a time and temperature shown in Table 3. After cooling, the prepared unreinforced catheter shaft section was longitudinally slit and flattened to provide a specimen suitable for a bond test. The results of the bond test are summarized in Table 3. The bond test, as will be shown herein, demonstrates that the application example tubes can produce a catheter shaft with a good bond to the liner without requiring an FEP heat shrink, e.g., comparable in some embodiments to conventional constructs (with non-recoverable, non-cross-linked outer sheath tubes and FEP heat shrink).

A specimen suitable for durometer hardness testing was prepared by compression molding dried pieces of Comparative Example 1 using a set point temperature of 380° F. and 15,000 pounds of clamping force to provide a plaque specimen of relatively uniform thickness. The durometer hardness was measured using a Type D indenter and the results are summarized in Table 4. There is a minimum thickness requirement for this test; accordingly, the tubes needed to be melted and pressed into a plaque. Comparative Example 1 (and 2) demonstrate that the application example tubes are non-crosslinked (as for Comparative Examples 1 and 2) since they form a plaque. Cross-linked materials cannot be melted and reformed, which is demonstrated by showing that a plaque could not be formed with Comparative Example 3 (which is crosslinked).

Comparative Example 2

A commercially available poly(ether-block-amide) (PEBA) resin (Arkema, Inc, PEBAX® 5533 SA 01 MED) was obtained in pellet form and dried in an oven at 158° F. overnight to ensure the resin moisture content was less than about 0.15% by weight. The dried resin was extruded into a tubular form using the same methods and conditions described in Comparative Example 1, except a die temperature of about 340° F. was used. The measured dimensional attributes of the produced non-crosslinked PEBA tubes are shown in Table 2.

A bond test specimen was prepared using the tube of Comparative Example 2 in an identical manner to the bond test specimen prepared using the tube of Comparative Example 1. The results of the bond test are summarized in Table 3.

A specimen suitable for durometer hardness testing using the tubes of Comparative Example 2 was prepared and measured in an identical manner to Comparative Example 1. The durometer hardness results are summarized in Table 4.

Comparative Example 3

A commercially available PEBA heat shrink tube manufactured by Cobalt Polymers (Part No. P2-140-006-CLR) that is marketed as a crosslinked 72 durometer Shore D PEBA heat shrink tube was purchased from Chamfr. The measured dimensional attributes before heating (i.e., as received), after heating (i.e., after being exposed to a recovery temperature for 10 minutes), and the calculated recovery properties of the crosslinked PEBA heat shrink tubes are summarized in Table 2. A bond test specimen was prepared using the tube of Comparative Example 3, without a FEP heat shrink fusing sleeve. The prepared unreinforced catheter shaft assembly was heated for a time and temperature shown in Table 3. After cooling, the prepared unreinforced catheter shaft section was longitudinally slit and flattened to provide a specimen suitable for a bond test. The results of the bond test are summarized in Table 3. An attempt was made to prepare a specimen suitable for durometer hardness testing using the tubes of Comparative Example 3 in an identical manner to Comparative Example 1. However, the specimen obtained by pressing the tubes of Comparative Example 3 at these conditions was very brittle after cooling and did not coalesce into a solid test specimen. The durometer hardness test was not performed on the specimen obtained from pressing Comparative Example 3 since a solid test specimen was not obtained. The PEBA heat shrink tubes of Comparative Example 3 are comprised of a crosslinked PEBA material, and therefore cannot be melted and reformed into a compression molded plaque.

Comparative Example 4

A commercially available PEBA heat shrink tube manufactured by Cobalt Polymers (Part No. P2-100-0025-CLR) that is marketed as a crosslinked 72 durometer Shore D PEBA heat shrink tube was purchased from Chamfr. The measured dimensional attributes before heating (i.e., as received), after heating (i.e., after being exposed to a recovery temperature for 10 minutes), and the calculated recovery properties of the crosslinked PEBA heat shrink tubes are summarized in Table 2. The PEBA heat shrink tubes of Comparative Example 4 are comprised of a crosslinked PEBA material, and therefore cannot be melted and reformed into a compression molded plaque.

Comparative Example 5

A commercially available PEBA heat shrink tube manufactured by Cobalt Polymers (Part No. P2-060-003-40-CLR) that is marketed as a crosslinked 40 durometer Shore D PEBA heat shrink tube was purchased from Chamfr. The measured dimensional attributes before heating (i.e., as received), after heating (i.e., after being exposed to a recovery temperature for 10 minutes), and the calculated recovery properties of the crosslinked PEBA heat shrink tubes are summarized in Table 2. The PEBA heat shrink tubes of Comparative Example 5 are comprised of a crosslinked PEBA material, and therefore cannot be melted and reformed into a compression molded plaque.

Example 1

A non-crosslinked PEBA input tube was prepared using the commercially available resin PEBAX® 7233 SA 01 MED (Arkema, Inc) using the same methods and conditions provided in Comparative Example 1, except a screw rotation of about 6 rpm and a DDR of about 10 was used. An input tube having an inner diameter of about 0.048", an average wall thickness of about 0.0145", and a concentricity of about 93% was obtained.

The prepared input tube was then expanded by pressurizing the inner diameter of the tube with compressed air as it is passed through a heated expansion die. The heated expansion die has openings along its inner surface that allows for pressurized air to circulate between the outer surface of the non-crosslinked PEBA input tube and the inner surface of the expansion die to maintain a specified expanded diameter. The processing parameters of expansion air pressure applied to the ID of the input tubing, temperature of the pressurized expansion air applied to the ID of the input tubing, expansion die air pressure, expansion die air temperature, expansion die air flowrate, linear tube throughput, cooling air temperature, and cooling air flowrate were all adjusted to give a non-crosslinked PEBA heat shrink tube according to the present disclosure.

In particular, the non-crosslinked PEBA heat shrink tube of Example 1 was expanded using an expansion die temperature of about 305° F. to about 310° F., an expansion air pressure of about 180 psi, a die air flowrate of about 2.3 cubic feet per minute (cfm) and a linear tube throughput of around 1.5 feet per minute (fpm).

The dimensional attributes of inner diameter and wall thickness of the expanded form of Example 1 were measured and the wall thickness concentricity was calculated. Three sections 2.5" long of the expanded non-crosslinked PEBA heat shrink tubing of Example 1 were cut and exposed to a recovery temperature for 10 minutes in a standard laboratory gravity convection oven. After allowing the lengths to cool to ambient temperature, the inner diameter, wall thickness, and length after heating were measured. The measured dimensional attributes before heating (i.e., expanded), after heating, and the calculated recovery properties of the non-crosslinked PEBA heat shrink tubes are summarized in Table 2.

A bond test specimen was prepared using the non-crosslinked PEBA heat shrink tube of Example 1, without a FEP heat shrink fusing sleeve. The prepared unreinforced catheter shaft assembly was heated for a time and temperature shown in Table 3. After cooling, the prepared unreinforced catheter shaft section was longitudinally slit and flattened to provide a specimen suitable for a bond test. The results of the bond test are summarized in Table 3.

Example 2

A PEBA input tube was prepared using the same materials, methods, and conditions provided in Example 1 to produce an input tube having identical dimensions to the input tube utilized in Example 1.

The prepared input tube was then expanded using the same methods and conditions as Example 1, except an expansion die temperature of about 310° F. to about 315° F., an expansion air pressure of about 187 psi, and a die air flowrate of about 2.1 cfm was used. The dimensional attributes of inner diameter and wall thickness of the expanded form of Example 2 were measured and the wall thickness concentricity was calculated. Three sections 2.5" long of the expanded non-crosslinked PEBA heat shrink tubing of Example 2 were cut and exposed to a recovery temperature for 10 minutes in a standard laboratory gravity convection oven. After allowing the lengths to cool to ambient temperature, the inner diameter, wall thickness, and length after heating were measured. The measured dimensional attributes before heating (i.e., expanded), after heating, and the calculated recovery properties of the non-crosslinked PEBA heat shrink tubes are summarized in Table 2.

A specimen suitable for durometer hardness testing using the expanded tubes of Example 2 was prepared and measured in an identical manner to Comparative Example 1. The durometer hardness results are summarized in Table 4.

Example 3

A non-crosslinked PEBA input tube was prepared using the commercially available resin PEBAX® 5533 SA 01 MED (Arkema, Inc) using the same methods and conditions provided in Comparative Example 2, except a screw rotation of about 6 rpm and a DDR of about 10 was used. An input tube having an inner diameter of about 0.051", an average wall thickness of about 0.0160", and a concentricity of about 97% was obtained.

The prepared input tube was then expanded using the same methods and conditions as Example 1, except an expansion die temperature of about 265° F. to about 275° F., an expansion air pressure of about 120 psi, and a die air flowrate of about 2.0 cfm was used. The dimensional attributes of inner diameter and wall thickness of the expanded form of Example 3 were measured and the wall thickness concentricity was calculated. Three sections 2.5" long of the expanded non-crosslinked PEBA heat shrink tubing of Example 3 were cut and exposed to a recovery temperature for 10 minutes in a standard laboratory gravity convection oven. After allowing the lengths to cool to ambient temperature, the inner diameter, wall thickness, and length after heating were measured. The measured dimensional attributes before heating (i.e., expanded), after heating, and the calculated recovery properties of the non-crosslinked PEBA heat shrink tubes are summarized in Table 2.

A bond test specimen was prepared using the non-crosslinked PEBA heat shrink tube of Example 3, without a FEP heat shrink fusing sleeve. The prepared unreinforced catheter shaft assembly was heated for a time and temperature shown in Table 3. After cooling, the prepared unreinforced catheter shaft section was longitudinally slit and flattened to provide a specimen suitable for a bond test. The results of the bond test are summarized in Table 3.

A specimen suitable for durometer hardness testing using the expanded tubes of Example 3 was prepared and measured in an identical manner to Comparative Example 1. The durometer hardness results are summarized in Table 4.

Example 4

A non-crosslinked PEBA input tube was prepared using the commercially available resin PEBAX® 4533 SA 01 MED (Arkema, Inc) obtained in pellet form and dried in an oven at 145° F. overnight to ensure the resin moisture content was less than about 0.15% by weight. The dried resin was extruded into a tubular form using the same methods and conditions described for preparation of the input tube for Example 2, except a die temperature of about 330° F. was used. An input tube having an inner diameter of about 0.048", an average wall thickness of about 0.0156", and a concentricity of about 96% was obtained.

The prepared input tube was then expanded using the same methods and conditions as Example 1, except an expansion die temperature of about 220° F. to about 235° F., an expansion air pressure of about 100 psi, and a die air flowrate of about 1.8 cfi was used. The dimensional attributes of inner diameter and wall thickness of the expanded form of Example 4 were measured and the wall thickness concentricity was calculated. Three sections 2.5" long of the expanded non-crosslinked PEBA heat shrink tubing of Example 4 were cut and exposed to a recovery temperature for 10 minutes in a standard laboratory gravity convection oven. After allowing the lengths to cool to ambient temperature, the inner diameter, wall thickness, and length after heating were measured. The measured dimensional attributes before heating (i.e., expanded), after heating, and the calculated recovery properties of the non-crosslinked PEBA heat shrink tubes are summarized in Table 2.

A bond test specimen was prepared using the non-crosslinked PEBA heat shrink tube of Example 4, without a FEP heat shrink fusing sleeve. The prepared unreinforced catheter shaft assembly was heated for a time and temperature shown in Table 3. After cooling, the prepared unreinforced catheter shaft section was longitudinally slit and flattened to provide a specimen suitable for a bond test. The results of the bond test are summarized in Table 3.

A specimen suitable for durometer hardness testing using the expanded tubes of Example 4 was prepared and measured in an identical manner to Comparative Example 1, except a set temperature of about 350° F. was used. The durometer hardness results are summarized in Table 4.

Example 5

A non-crosslinked PEBA input tube was prepared using the commercially available resin PEBAX® 3533 SA 01 MED (Arkema, Inc) obtained in pellet form and dried in an oven at 140° F. overnight to ensure the resin moisture content was less than about 0.15% by weight. The dried resin was extruded into a tubular form using the same methods and conditions described for preparation of the input tube for Example 4, except a except a screw rotation of about 8 rpm was used. An input tube having an inner diameter of about 0.048", an average wall thickness of about 0.0155", and a concentricity of about 96% was obtained.

The prepared input tube was then expanded using the same methods and conditions as Example 1, except an expansion die temperature of about 180° F. to about 205° F., an expansion air pressure of about 55 psi, and a die air flowrate of about 1.9 cfm was used. The dimensional attributes of inner diameter and wall thickness of the expanded form of Example 5 were measured and the wall thickness concentricity was calculated. Three sections 2.5" long of the expanded non-crosslinked PEBA heat shrink tubing of Example 5 were cut and exposed to a recovery temperature for 10 minutes in a standard laboratory gravity convection oven. After allowing the lengths to cool to ambient temperature, the inner diameter, wall thickness, and length after heating were measured. The measured dimensional attributes before heating (i.e., expanded), after heating, and the calculated recovery properties of the non-crosslinked PEBA heat shrink tubes are summarized in Table 2.

Example 6

A non-crosslinked PEBA input tube was prepared using the same materials, methods, and conditions provided in Example 5, except a DDR of about 9 and a screw rotation of about 7 rpm was used. An input tube having an inner diameter of about 0.062", an average wall thickness of about 0.0150", and a concentricity of about 85% was obtained.

The prepared input tube was then expanded using the same methods and conditions as Example 5, except an expansion die temperature of about 180° F. to about 210° F., an expansion air pressure of about 40 psi, and a die air flowrate of about 1.7 cfm was used. The dimensional attributes of inner diameter and wall thickness of the expanded form of Example 6 were measured and the wall thickness concentricity was calculated. Three sections 2.5" long of the expanded non-crosslinked PEBA heat shrink tubing of Example 6 were cut and exposed to a recovery temperature for 10 minutes in a standard laboratory gravity convection oven. After allowing the lengths to cool to ambient temperature, the inner diameter, wall thickness, and length after heating were measured. The measured dimensional attributes before heating (i.e., expanded), after heating, and the calculated recovery properties of the non-crosslinked PEBA heat shrink tubes are summarized in Table 2.

A specimen suitable for durometer hardness testing using the expanded tubes of Example 6 was prepared and measured in an identical manner to Example 4. The durometer hardness results are summarized in Table 4.

Example 7

A non-crosslinked PEBA input tube was prepared using the commercially available resin PEBAX® 2533 SA 01 MED (Arkema, Inc) obtained in pellet form and dried in an oven at 125° F. overnight to ensure the resin moisture content was less than about 0.15% by weight. The dried resin was extruded into a tubular form using the same methods and conditions described for preparation of the input tube for Example 5, except a screw rotation of about 5 rpm and a die temperature of about 280° F. was used. An input tube having an inner diameter of about 0.048", an average wall thickness of about 0.0154", and a concentricity of about 89% was obtained.

The prepared input tube was then expanded using the same methods and conditions as Example 6, except an expansion die temperature of about 165° F. to about 190° F. and an expansion air pressure of about 48 psi was used. The dimensional attributes of inner diameter and wall thickness of the expanded form of Example 7 were measured and the wall thickness concentricity was calculated. Three sections 2.5" long of the expanded non-crosslinked PEBA heat shrink tubing of Example 7 were cut and exposed to a recovery temperature for 10 minutes in a standard laboratory gravity convection oven. After allowing the lengths to cool to ambient temperature, the inner diameter, wall thickness, and length after heating were measured. The measured dimensional attributes before heating (i.e., expanded), after heating, and the calculated recovery properties of the non-crosslinked PEBA heat shrink tubes are summarized in Table 2.

A specimen suitable for durometer hardness testing using the expanded tubes of Example 6 was prepared and measured in an identical manner to Example 4. The durometer hardness results are summarized in Table 4.

Example 8

A non-crosslinked PEBA input tube was prepared using the same materials, methods, and conditions provided in Example 3, except a screw rotation of about 2 rpm and a DDR of about 4 was used. An input tube having an inner diameter of about 0.024", an average wall thickness of about 0.0077", and a concentricity of about 85% was obtained.

The prepared input tube was then expanded using the same methods and conditions as Example 3, except an expansion air pressure of about 105 psi was used. The dimensional attributes of inner diameter and wall thickness of the expanded form of Example 8 were measured and the wall thickness concentricity was calculated. Three sections 2.5" long of the expanded non-crosslinked PEBA heat shrink tubing of Example 8 were cut and exposed to a recovery temperature for 10 minutes in a standard laboratory gravity convection oven. After allowing the lengths to cool to ambient temperature, the inner diameter, wall thickness, and length after heating were measured. The measured dimensional attributes before heating (i.e., expanded), after heating, and the calculated recovery properties of the non-crosslinked PEBA heat shrink tubes are summarized in Table 2.

The expanded non-crosslinked PEBA heat shrink tubing of Example 8 was subsequently used in the fabrication of Example 11 and Comparative Example 7, as described below.

Example 9

A PEBA input tube was prepared using the same materials, methods, and conditions provided in Example 3 to produce an input tube having identical dimensions to the input tube utilized in Example 3.

The prepared input tube was then expanded using the same methods and conditions as Example 3, except an expansion air pressure of about 110 psi was used. The dimensional attributes of inner diameter and wall thickness of the expanded form of Example 9 were measured and the wall thickness concentricity was calculated. Three sections 2.5" long of the expanded non-crosslinked PEBA heat shrink tubing of Example 9 were cut and exposed to a recovery temperature for 10 minutes in a standard laboratory gravity convection oven. After allowing the lengths to cool to ambient temperature, the inner diameter, wall thickness, and length after heating were measured. The measured dimensional attributes before heating (i.e., expanded), after heating, and the calculated recovery properties of the non-crosslinked PEBA heat shrink tubes are summarized in Table 2.

The expanded non-crosslinked PEBA heat shrink tubing of Example 9 was subsequently used in the fabrication of Example 10 and Comparative Example 6, as described below.

Example 10

A commercially available 5 French (0.065" OD) laser-cut flexible hypotube (Part No. AD_043750 manufactured by Resonetics, Inc.) was purchased from Chamfr to assemble a covered laser-cut hypotube. The 5 Fr laser-cut hypotube was used as received and not modified in any way. The 5 Fr laser-cut hypotube was inserted into a length of the expanded non-crosslinked PEBA heat shrink tube of Example 9. This assembly (i.e., the laser-cut hypotube and non-crosslinked PEBA heat shrink tube of Example 9) was suspended vertically and heated in a Beahm 815A vertical laminator equipped with an enclosed circular thermal nozzle with 0.5" openings set at 300° F. at a traverse rate of 2.2 mm/s. After cooling, the completed build was examined using a Keyence VHX-5000 digital microscope to determine if the non-crosslinked PEBA heat shrink tube flowed within the laser-cut interstices of the hypotube during the recovery process. The center portion of the covered laser-cut hypotube was bent into a U-shape and secured on the microscope stage during the examination. Images captured during this examination are shown in FIG. 5, the results from which are summarized in Table 6.

Comparative Example 6

A covered laser-cut hypotube was prepared using a 5 French laser-cut hypotube (identical to the hypotube used in the fabrication of Example 10) purchased from Chamfr. Comparative Example 6 was prepared in a similar fashion to Example 10 by sliding the laser-cut hypotube into a length of the expanded non-crosslinked PEBA heat shrink tube of Example 9, except an FEP heat shrink fusing sleeve having an expanded diameter of about 0.100", a wall thickness of about 0.0090", and a recovered inner diameter of about 0.063" was placed over the assembly (i.e., over the non-crosslinked PEBA heat shrink tube of Example 9) before heating. The recovery ratio and dimensional attributes of the FEP heat shrink sleeve utilized was selected based on typical dimensional considerations for a traditional catheter reflow process 10. The assembly was then suspended in the vertical laminator and heated in a similar fashion to Example 9, with the exception of nozzle temperature and traverse rate which were set at typical conditions for reflow processes 10 involving an FEP fusing sleeve. The nozzle temperature was set at 480° F. and a traverse rate of 1.2 mm/s was used. After cooling, the completed build was examined using a Keyence VHX-5000 digital microscope in an identical manner to the examination performed on Example 10. Images captured during this examination are shown in FIG. 6, the results from which are summarized in Table 6.

Example 11

A commercially available 2.75 French (0.036" OD) laser-cut flexible hypotube (Part No. KTSS0004 manufactured by Lumenous Device Technologies) was purchased from Chamfr to assemble a covered laser-cut hypotube. The 2.75 Fr laser-cut hypotube was used as received and not modified in any way. The 2.75 Fr laser-cut hypotube was inserted into a length of the expanded non-crosslinked PEBA heat shrink tube of Example 8. This assembly (i.e., the laser-cut hypotube and non-crosslinked PEBA heat shrink tube of Example 8) was suspended in the vertical laminator and heated using similar conditions to Example 10, except a traverse rate of 6.2 mm/s was used. After cooling, the completed build was examined using a Keyence VHX-5000 digital microscope in an identical manner to the examination performed on Example 10. Images captured during this examination are shown in FIG. 7, the results from which are summarized in Table 6.

Comparative Example 7

A covered laser-cut hypotube was prepared using a 2.75 French laser-cut hypotube (identical to the hypotube used in the fabrication of Example 11) purchased from Chamfr. Comparative Example 7 was prepared in a similar fashion to Example 11 by sliding the laser-cut hypotube into a length of the expanded non-crosslinked PEBA heat shrink tube of Example 8, except an FEP heat shrink fusing sleeve having an expanded diameter of about 0.056", a wall thickness of about 0.0080", and a recovered inner diameter of about 0.035" was placed over the assembly (i.e., over the non-crosslinked PEBA heat shrink tube of Example 8) before heating. The recovery ratio and dimensional attributes of the FEP heat shrink sleeve utilized was selected based on typical dimensional considerations for a traditional catheter reflow process 10. The assembly was then suspended in the vertical laminator and heated in a similar fashion to Example 11, with the exception of nozzle temperature and traverse rate which were set at typical conditions for reflow processes 10 involving an FEP fusing sleeve. The nozzle temperature was set at 480° F. and a traverse rate of 1.2 mm/s was used. After cooling, the completed build was examined using a Keyence VHX-5000 digital microscope in an identical manner to the examination performed on Example 10. Images captured during this examination are shown in FIG. 8, the results from which are summarized in Table 6.

Example 12

Figure 9:
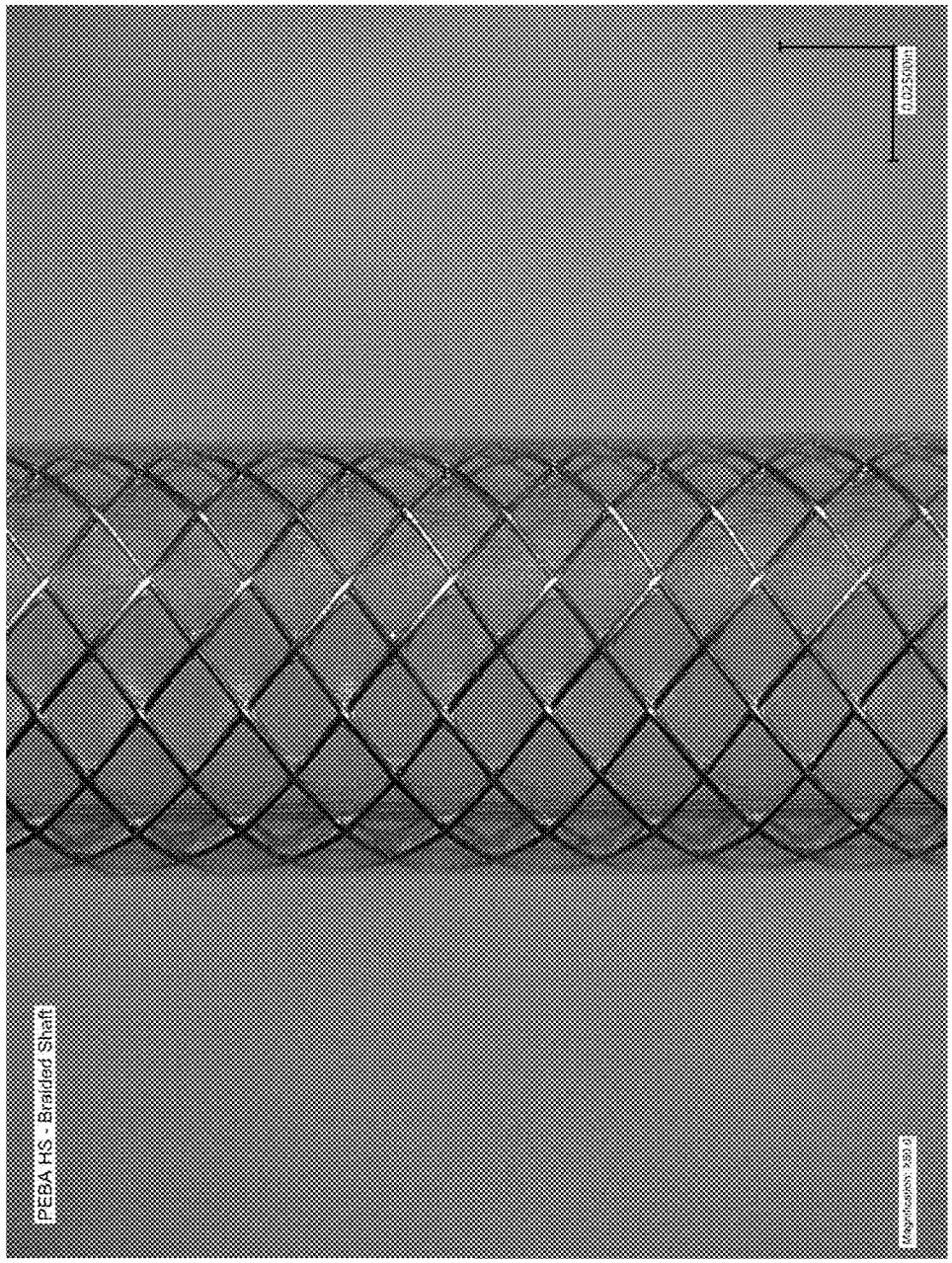
FIG. 9 is a ×50 magnification microscopic image captured during the examination of Example 12—a braid reinforced catheter shaft that was covered with using the recovery method 20 with the non-crosslinked PEBA heat shrink tube of Example 4.

A braid reinforced PTFE liner was fabricated by placing an outer surface modified PTFE liner tube with an inner diameter of 0.067" and a wall thickness of 0.0025" over a 0.065" stainless steel mandrel. The PTFE liner tube was stretched by hand at room temperature so that it fit snugly over the stainless-steel mandrel. Afterwards, 0.002" OD stainless-steel wire acquired from Fort Wayne Metals Research Products, LLC was used to form a 16-carrier braid reinforcement over the PTFE liner in a full load pattern at 45 PPI (picks-per-inch) using a Steeger USA K80 Series horizontal braider. The stainless-steel braid reinforced liner was then inserted into a length of the expanded non-crosslinked PEBA heat shrink tube of Example 4. This assembly (i.e., the braid reinforced liner and non-crosslinked PEBA heat shrink tube of Example 4) was suspended vertically and heated in a Beahm 815A vertical laminator equipped with an enclosed circular thermal nozzle with 0.5" openings set at 400° F. at a traverse rate of 1.2 mm/s to provide a braid reinforced catheter shaft with an outer jacket comprising non-crosslinked PEBA heat shrink tubing. After cooling, the completed build was examined using a Keyence VHX-5000 digital microscope to determine if the non-crosslinked PEBA heat shrink tube flowed within the interstices of the braid reinforcement and made adequate contact with the outer surface of the inner liner during the heating process. Images captured during this examination are shown in FIG. 9.

Comparative Example 8

Figure 10:
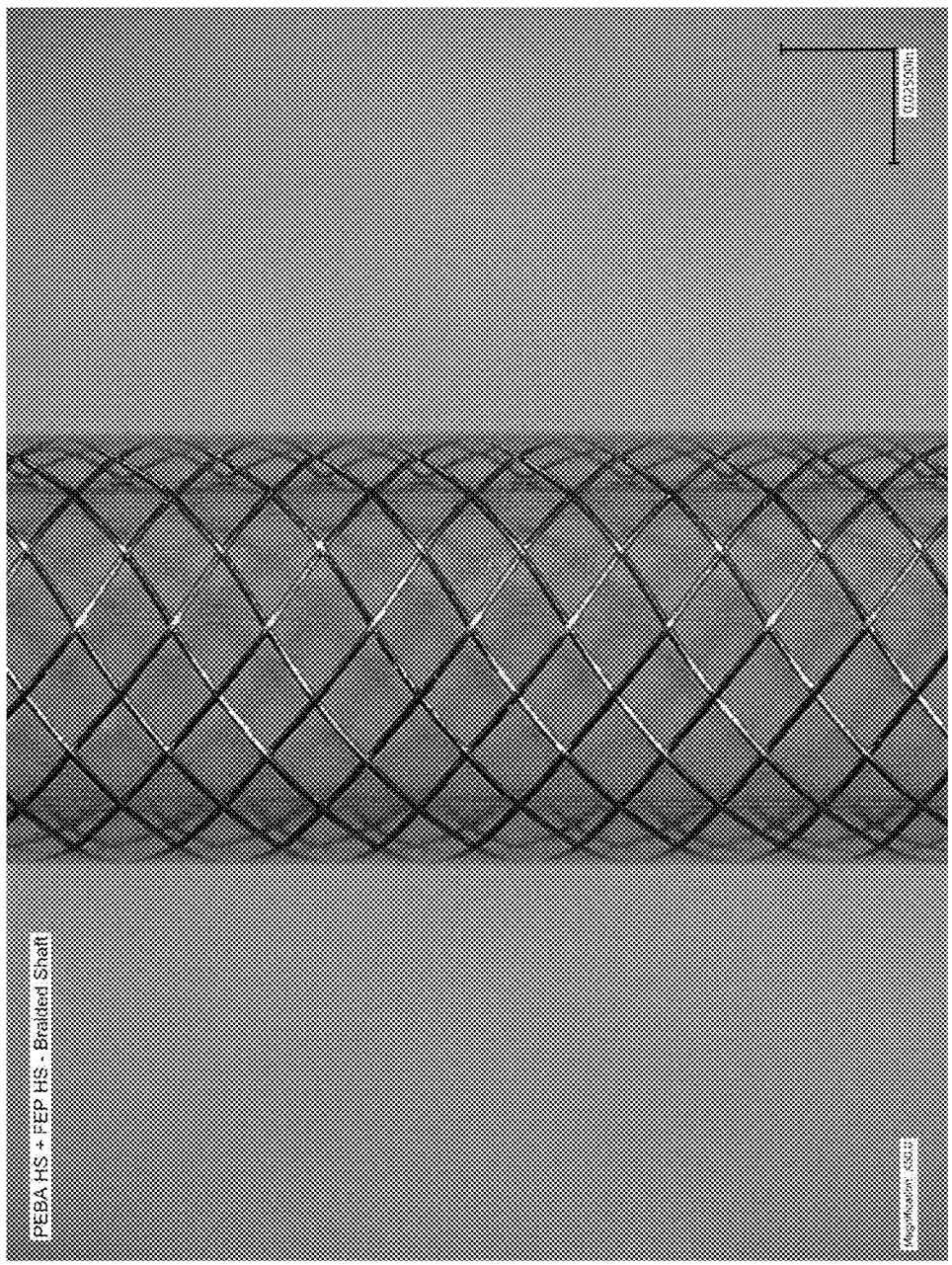
FIG. 10 is a ×50 magnification microscopic image captured during the examination of Comparative Example 8—a braid reinforced catheter shaft that was covered using the traditional reflow method 10 with the non-crosslinked PEBA heat shrink tube of Example 4 and an appropriately sized FEP heat shrink fusing sleeve. The FEP heat shrink fusing sleeve was skived from the build before microscopic examination.

A braid reinforced PTFE liner was fabricated using the same materials and conditions described in Example 12. Comparative Example 8 was prepared in a similar fashion to Example 12 by sliding the stainless-steel braid reinforced liner into a length of the expanded non-crosslinked PEBA heat shrink tube of Example 4, except an FEP heat shrink fusing sleeve having an expanded diameter of about 0.100", a wall thickness of about 0.0090", and a recovered inner diameter of about 0.063" was placed over the assembly (i.e., over the non-crosslinked PEBA heat shrink tube of Example 4) before heating. The recovery ratio and dimensional attributes of the FEP heat shrink sleeve utilized was selected based on typical dimensional considerations for a traditional catheter reflow process 10. The assembly was then suspended in the vertical laminator and heated in a similar fashion to Example 12, with the exception of nozzle temperature and traverse rate which were set at typical conditions for reflow processes 10 involving an FEP fusing sleeve. The nozzle temperature was set at 480° F. and a traverse rate of 1.2 mm/s was used. After cooling, the completed build was examined using a Keyence VHX-5000 digital microscope in an identical manner to the examination performed on Example 12. Images captured during this examination are shown in FIG. 10.

Cumulative Results

Table 2 summarizes the measured tubular dimensions of the PEBA tubes of Comparative Examples 1-5 and Examples 1-8. The dimensional attributes measured "Before Heating" include the as prepared inner diameter (i.e., the as extruded ID for the non-heat shrinkable tubes of Comparative Examples 1-2, the as received expanded ID for the heat shrinkable tubes of Comparative Examples 3-5, or the expanded ID for the non-crosslinked PEBA heat shrinkable tubes of Examples 1-9), the average wall thickness (denoted as "wt"), and the percent concentricity of the wall thickness. A total of four inner diameter and wall thickness measurements were taken on each specimen optically using a Keyence VHX-5000 digital microscope on a cross-section cut from the Examples. Both the inner diameter and wall thickness was measured in units of inches. The concentricity is expressed as a percentage, and was calculated by dividing the minimum (i.e., thinnest) wall thickness measurement observed by the maximum (i.e., thickest) wall thickness measurement observed and multiplying the resulting value by 100. The values shown in Table 2 are an average of 3 replicates.

TABLE 2

Dimensional Attributes of the Examples

| Example | Before Heating ID [in] | Before Heating wt [in] | Before Heating Conc. [%] | Recovery Temp. [° F.] | After Heating (10 min) ID [in] | After Heating (10 min) wt [in] | After Heating (10 min) Conc. [%] | Recovery Properties RR | Recovery Properties ΔID [%] | Recovery Properties ΔL [%] |
|---|---|---|---|---|---|---|---|---|---|---|
| Comp. 1 | 0.085 | 0.0065 | 96 | — | — | — | — | — | — | — |
| Comp. 2 | 0.085 | 0.0055 | 93 | — | — | — | — | — | — | — |
| Comp. 3 | 0.157 | 0.0028 | 74 | 340 | 0.072 | 0.0060 | 90 | 2.19 | 54 | −8.5 |
| Comp. 4 | 0.108 | 0.0016 | 58 | 340 | 0.079 | 0.0022 | 68 | 1.37 | 27 | −6.1 |
| Comp. 5 | 0.067 | 0.0014 | 84 | 340 | 0.033 | 0.0023 | 88 | 2.02 | 50 | −2.8 |
| Ex. 1 | 0.088 | 0.0097 | 90 | 320 | 0.075 | 0.0111 | 94 | 1.16 | 14 | 0.0 |
| Ex. 2 | 0.109 | 0.0080 | 92 | 320 | 0.089 | 0.0096 | 95 | 1.22 | 18 | −1.3 |
| Ex. 3 | 0.087 | 0.0101 | 92 | 300 | 0.071 | 0.0120 | 91 | 1.23 | 18 | −1.3 |
| Ex. 4 | 0.093 | 0.0097 | 94 | 270 | 0.068 | 0.0131 | 94 | 1.36 | 27 | −3.8 |
| Ex. 5 | 0.080 | 0.0107 | 95 | 260 | 0.056 | 0.0148 | 95 | 1.42 | 29 | −7.5 |
| Ex. 6 | 0.089 | 0.0113 | 79 | 260 | 0.070 | 0.0141 | 83 | 1.27 | 21 | −5.0 |
| Ex. 7 | 0.072 | 0.0115 | 88 | 220 | 0.055 | 0.0150 | 90 | 1.32 | 24 | −8.8 |
| Ex. 8 | 0.043 | 0.0053 | 72 | 300 | 0.035 | 0.0060 | 73 | 1.24 | 20 | −2.5 |
| Ex. 9 | 0.074 | 0.0114 | 96 | 300 | 0.063 | 0.0124 | 97 | 1.16 | 14 | 0.0 |

TABLE 3

Bond Test Results

| Example | Oven Temperature [° F.] | Time [min] | Peel Mode |
|---|---|---|---|
| Comp. 1 | 410 | 5 | + |
| Comp. 2 | 410 | 5 | + |
| Comp. 3* | 340 | 5 | +− |
| Ex. 1 | 350 | 5 | + |
| Ex. 3 | 350 | 5 | + |
| Ex. 4 | 310 | 5 | + |

+ Cohesive peel mode at interface of PTFE liner and PEBA outer jacket when peeled
− Adhesive peel mode at interface of PTFE liner and PEBA outer jacket when peeled
*Both peel modes were observed intermittently for Comp. 3

TABLE 4

Durometer Hardness (Shore D)

| Example | Comp. 1 | Comp. 2 | Comp. 3 | Ex. 2 | Ex. 3 | Ex. 4 | Ex. 6 | Ex. 7 |
|---|---|---|---|---|---|---|---|---|
| Hardness | 56 | 48 | # | 60 | 50 | 42 | 30 | 24 |

Tubes did not coalesce into a solid test specimen after pressing

TABLE 5

Covered Laser Cut Hypotube Microscopic Examination

| | Examination Location | |
|---|---|---|
| Example | Outer Surface | Laser Cut Gap |
| Ex. 10 | ∩ | = ] |
| Comp. 6 | ≈ | ≠ > |
| Ex. 11 | ∩ | = ] |
| Comp. 7 | ≈ | ≠ > |

≈ Undulating outer surface when bent into U-shape
≠ Cracks when bent into U-shape
> Infiltrates laser-cut gap
∩ Smooth outer surface when bent into U-shape
= Does not crack when bent into U-shape
] Does not infiltrate laser-cut gap

What is claimed is:

1. A heat shrink tubing comprising non-crosslinked PEBA, wherein the heat shrink tubing has a recovery ratio (RR) greater than about 1.05:1 and/or is reducible in internal diameter (ID) by about 4.8%, wherein the heat shrink tubing comprises less than 2% by weight of crosslinked polymer.

2. The heat shrink tubing of claim 1, consisting essentially of the non-crosslinked PEBA.

3. The heat shrink tubing of claim 1, wherein the RR is greater than about 1.10:1 and/or is reducible in ID by about 9.1%.

4. The heat shrink tubing of claim 1, wherein the RR is greater than about 1.2:1 and/or is reducible in ID by about 16.7%.

5. The heat shrink tubing of claim 1, wherein the RR is greater than about 1.3:1 and/or reducible in ID by about 23.1%.

6. The heat shrink tubing of claim 1, wherein the RR is greater than about 1.4:1 and/or reducible in ID by about 28.6%.

7. The heat shrink tubing of claim 1, wherein the RR is greater than about 1.5:1 and/or reducible in ID by about 33.3%.

8. The heat shrink tubing of claim 1, wherein the RR is greater than about 1.6:1 and/or reducible in ID by about 37.5%.

9. The heat shrink tubing of claim 1, wherein a durometer hardness measurement according to ASTM D2240 conducted on a flat specimen fabricated by melt pressing the heat shrink tubing in expanded form is about 20 to 80 Shore D.

10. The heat shrink tubing of claim 1, further comprising a liquid or polymeric coating on an outer surface of the tubing that enhances the lubricity or chemical resistance of the tubing.

11. The heat shrink tubing of claim 10, wherein the liquid or polymeric coating is hydrophobic.

12. A catheter comprising the heat shrink tubing of claim 1.

13. The catheter of claim 12, selected from the group consisting of a guide catheter, microcatheter, balloon catheter, and steerable delivery catheter.

* * * * *